(12) United States Patent
Goldfine et al.

(10) Patent No.: US 7,812,601 B2
(45) Date of Patent: Oct. 12, 2010

(54) MATERIAL CONDITION ASSESSMENT WITH EDDY CURRENT SENSORS

(75) Inventors: Neil J. Goldfine, Newton, MA (US); Andrew P. Washabaugh, Chula Vista, CA (US); Yanko K. Sheiretov, Waltham, MA (US); Darrell E. Schlicker, Watertown, MA (US); Robert J. Lyons, Boston, MA (US); Mark D. Windoloski, Chelmsford, MA (US); Christopher A. Craven, Bedford, MA (US); Vladimir B. Tsukernik, West Roxbury, MA (US); David C. Grundy, Reading, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 0 days.

(21) Appl. No.: 12/484,761

(22) Filed: Jun. 15, 2009

(65) Prior Publication Data
US 2010/0026285 A1 Feb. 4, 2010

Related U.S. Application Data

(62) Division of application No. 11/343,741, filed on Jan. 30, 2006, now abandoned.

(60) Provisional application No. 60/647,979, filed on Jan. 28, 2005, provisional application No. 60/648,759, filed on Feb. 1, 2005, provisional application No. 60/727,699, filed on Oct. 17, 2005.

(51) Int. Cl.
*G01N 27/72* (2006.01)
*G01N 27/90* (2006.01)

(52) U.S. Cl. .................. 324/238; 324/235; 324/209

(58) Field of Classification Search ................ 324/209, 324/235, 238
See application file for complete search history.

(56) References Cited

U.S. PATENT DOCUMENTS 5,015,951 A   5/1991   Melcher (Continued)

OTHER PUBLICATIONS

Blodgett, M.P., Ukpabi, C.V., and Nagy, P.B., "Surface Roughness Influence on Eddy Current Electrical Conductivity Measurements," Materials Evaluation, pp. 765-772 Jun. 2003.

(Continued)

*Primary Examiner*—Reena Aurora
(74) *Attorney, Agent, or Firm*—Hamilton, Brook, Smith & Reynolds, P.C.

(57) ABSTRACT

Eddy current sensors and sensor arrays are used for process quality and material condition assessment of conducting materials. In an embodiment, changes in spatially registered high resolution images taken before and after cold work processing reflect the quality of the process, such as intensity and coverage. These images also permit the suppression or removal of local outlier variations. Anisotropy in a material property, such as magnetic permeability or electrical conductivity, can be intentionally introduced and used to assess material condition resulting from an operation, such as a cold work or heat treatment. The anisotropy is determined by sensors that provide directional property measurements. The sensor directionality arises from constructs that use a linear conducting drive segment to impose the magnetic field in a test material. Maintaining the orientation of this drive segment, and associated sense elements, relative to a material edge provides enhanced sensitivity for crack detection at edges.

18 Claims, 22 Drawing Sheets

U.S. PATENT DOCUMENTS

| | | | |
|---|---|---|---|
| 5,172,580 A * | 12/1992 | Thompson | 72/53 |
| 5,453,689 A | 9/1995 | Goldfine et al. | |
| 5,793,206 A | 8/1998 | Goldfine et al. | |
| RE36,986 E | 12/2000 | Melcher | |
| 6,188,218 B1 | 2/2001 | Goldfine et al. | |
| 6,657,429 B1 | 12/2003 | Goldfine et al. | |
| 6,952,095 B1 | 10/2005 | Goldfine et al. | |
| 6,992,482 B2 | 1/2006 | Shay et al. | |
| 7,161,350 B2 | 1/2007 | Goldfine et al. | |
| 7,289,913 B2 | 10/2007 | Schlicker et al. | |
| 7,451,657 B2 * | 11/2008 | Goldfine et al. | 73/760 |
| 2003/0164700 A1 | 9/2003 | Goldfine et al. | |
| 2007/0069720 A1 | 3/2007 | Goldfine et al. | |

OTHER PUBLICATIONS

Goldfine, N., "Characterization of Shot Peening using Eddy Current MWM Sensors and Imaging MWM-Arrays," 2004 U.S. Shot Peening and Blast Cleaning Workshop Presentation, Dearborn, MI, Oct. 2004, 72 pages.

* cited by examiner

Drive at Angle to Crack = Medium Detection Sensitivity, High Image Resolution

Crack at Edge = High Detection Sensitivity (at edge), High Image Resolution (at edge)

MATERIAL CONDITION ASSESSMENT WITH EDDY CURRENT SENSORS

RELATED APPLICATIONS

This application is a divisional of U.S. application Ser. No. 11/343,741, filed Jan. 30, 2006, now abandoned which claims the benefit of U.S. Provisional Application Nos. 60/647,979 filed Jan. 28, 2005, 60/648,759 filed Feb. 1, 2005, and 60/727,699 filed Oct. 17, 2005.

The entire teachings of the above applications are incorporated herein by reference.

GOVERNMENT SUPPORT

The invention was supported, in whole or in part, by Prime Contract Number NAS9-20000 from NASA. The Government has certain rights in the invention.

BACKGROUND OF THE INVENTION

The technical field of this invention is that of nondestructive materials characterization, particularly quantitative, model-based characterization of surface, near-surface, and bulk material condition for flat and curved parts or components. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing the material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution. Spatially periodic field eddy-current sensors have been used to measure foil thickness, characterize coatings, and measure porosity, as well as to measure property profiles as a function of depth into a part, as disclosed in U.S. Pat. Nos. 5,015,951 and 5,453,689.

A common inspection technique, termed conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks. A particular difficulty with eddy current sensors is the effect of material discontinuities, such as edges of the material. These edges can strongly influence the response of the sensor and potentially mask the response of cracks that commonly form at these edges.

Attempts have been made to use these sensors to assess the quality of a shot peening process applied to metals. This process involves cold working the material surface and introduces compressive stresses at the surface of a material in order to help prevent the formation of cracks. Shot peening also affects the roughness of the material surface, which can affect eddy current sensor measurements of the material properties such as the effective electrical conductivity [Blodgett, 2003]. Relatively large footprint sensors that try to average out roughness variations have only had limited success in assessing the cold work quality after the process has been performed. Correction algorithms to account for the surface roughness effect on the electrical property measurements have also been developed [Goldfine, 2004].

SUMMARY OF THE INVENTION

Aspects of the methods described herein involve nondestructive evaluation of materials for the assessment of operations performed on the material and also the detection of local features, such as cracks, that may occur at the edges of the test material.

In an embodiment, the quality of a cold work process is assessed by changes in spatially registered high resolution responses obtained with eddy current sensors or sensor arrays before and after processing. These responses, in one or two spatial dimensions, reflect the eddy current sensor or array response at a plurality of locations along the material surface and the spatial registration ensures that local property variations or inhomogeneities in the material itself are aligned when the responses are compared. This comparison, which can be a simple difference in the responses, can be used to suppress or remove local outlier responses that would otherwise skew an average or more global response for a given material position or area. In an embodiment, the cold work process is shot peening and the sensor response is a two-dimensional image of a property. The process quality can be reflected in terms of the coverage of the cold work process, through correlations with an alternate scale for the process, such as a residual stress measurement or Almen intensity, or through uniformity of the cold work intensity.

In an embodiment the material is a nickel alloy. In other embodiments, single or multiple excitation frequencies are used to interrogate the test material. In yet another embodiment, the sensor response compensates for variations in surface roughness associated with the process. The sensor response can be converted into material properties, such as a magnetic permeability or electrical conductivity, using a physics-based model. Preferably, the conversion uses a pre-computed database of sensor responses. In an embodiment, the sensor is a flexible array that can conform to the shape of the test material. In a specific embodiment, the test material is an engine disk slot and the sensor response is a two-dimensional image of a property that can be related to the cold work quality.

In another embodiment, variations in the anisotropic or directionally dependent material properties are used to assess a material condition or the quality of an operation. Measurements are performed before and after the operation or exposure to service conditions to determine changes in the anisotropic properties. These changes can reflect microstructural changes in the material, due, for example, from a heat treatment where the thermal exposure was above a specified level. In particular, for a nickel alloy a temperature exposure of 650° C. for at least 48 hours will lead to microstructural changes in the alloy that also affect the anisotropy of the properties. In contrast, a heat treatment at lower temperatures or shorter times may the residual stress in the material, but not alter the microstructure. In an embodiment, the operation is a shot peening process and the material is titanium. In another embodiment, the anisotropic properties are measured with an eddy current sensor capable of measuring directionally dependent properties. In these embodiments, prior to the operation or exposure, the material is preconditioned, possibly with a mechanical overload action, to intentionally introduce anisotropy in the material properties.

In yet another embodiment, cracks near material edges are detected with an eddy current sensor having at least one linear conducting segment for imposing a magnetic field in a test material when driven by a time varying electric current. A sense element is positioned near this drive conductor to provide a response to the magnetic field and reflects the material condition as the sensor is scanned along the edge. By maintaining the orientation of the conducting drive segment relative to the edge while the sensor is scanned, complex edge shapes, such as slots, can be inspected for the presence of cracks. Preferably, the linear drive segment is oriented at or nearly perpendicular to the edge. In an embodiment, the sense element is only partially over the test material and straddles the edge. In another embodiment, a sensor array is used where a plurality of sense elements are positioned parallel to the linear drive conductor. In yet another embodiment, a library of crack signature responses, which had previously been stored, are used to filter the sensor response when scanning a component material.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 25 shows a representative data for a sensor array scanned along an edge with an offset of 0.0 in.;

FIG. 26 shows a representative data for a sensor array scanned along an edge with an offset of 0.01 in.;

FIG. 27 shows a representative data for a sensor array scanned along an edge with an offset of 0.02 in.;

FIG. 28 shows a representative data for a sensor array scanned along an edge with an offset of 0.03 in.;

FIG. 29 shows a representative data for a sensor array scanned along an edge with an offset of 0.04 in.;

FIG. 30 shows a representative data for a sensor array scanned along an edge with an offset of 0.05 in.;

DETAILED DESCRIPTION OF THE INVENTION

A description of preferred embodiments of the invention follows.

This invention is directed toward an assessment of material condition due to processing or in-service usage as well as the detection of the cracks at edges of metallic materials. This is accomplished through the use of eddy current sensors and sensor arrays that can provide high spatial resolution sensor responses in one or two dimensions and anisotropic or direction-dependent material property measurements. The use of models that can rapidly and accurately predict the sensor response allows measured sensor responses to be converted into estimates of effective properties that can characterize the test material. These effective properties of the test material include the electrical conductivity and magnetic permeability as well as the thicknesses of material layers, such as a lift-off or sensor proximity. The sensor responses and effective properties reflect the cold working process and the anisotropic variation in these properties can be used to reflect the process quality or operational exposure. Furthermore, the detection of cracks at edges of material can be improved by using directionally dependent sensors.

Figure 1:
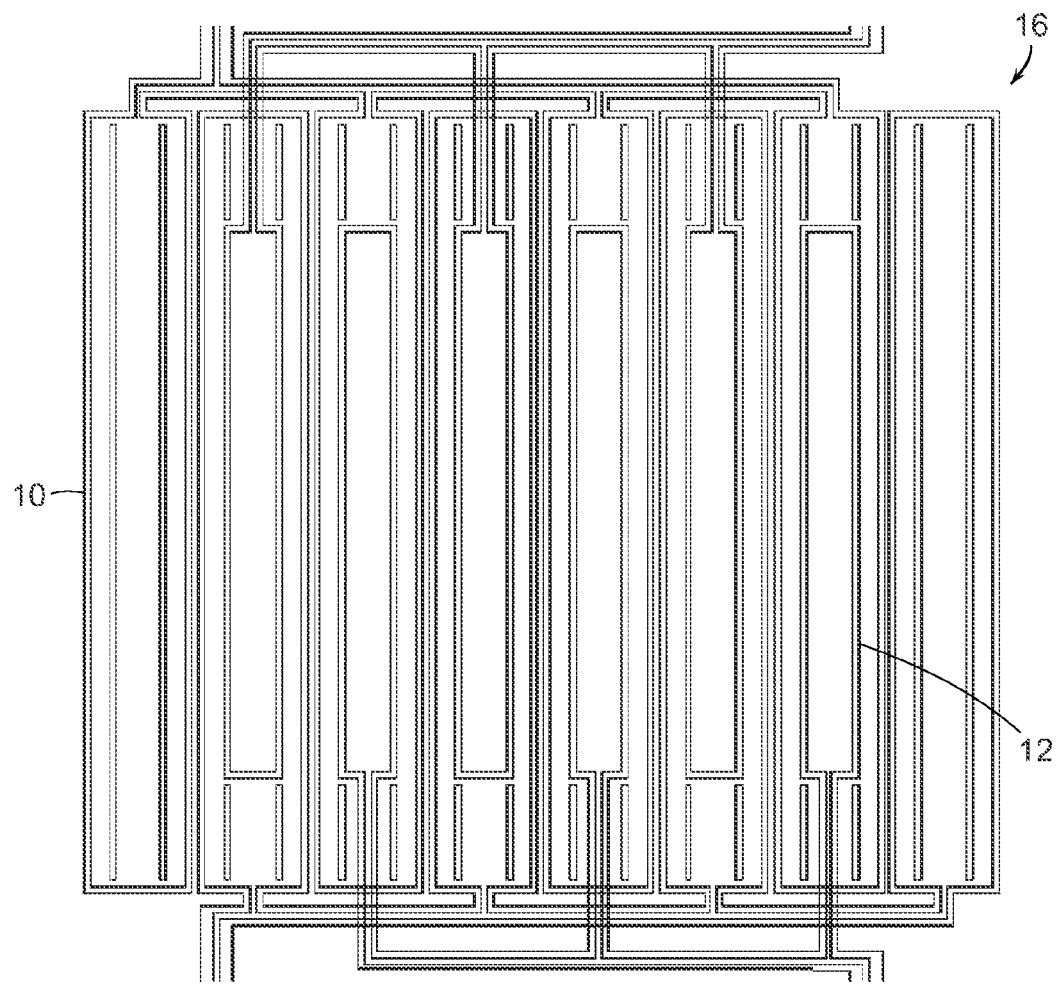
FIG. 1 shows a drawing of a spatially periodic field eddy-current sensor.

An example magnetic field based sensor that operates in the magnetoquasistatic regime and is well-suited to this approach is shown in FIG. 1. This meandering winding magnetometer (MWM®) is a "planar," conformable eddy-current sensor that was designed to support quantitative and autonomous data interpretation methods. The sensor 16 is described in U.S. Pat. Nos. 5,453,689, 5,793,206, 6,188,218, 6,657,429 and U.S. patent application Ser. No. 09/666,524 filed on Sep. 20, 2000 and Ser. No. 09/633,905 filed Aug. 4, 2003, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength $\lambda$. A current is applied to the primary winding to create a magnetic field and the response of the MUT to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. Nos. 5,793,206 and Re. 36,986.

The MWM-Arrays typically have one or more drive windings, possibly a single rectangle, and multiple sensing elements for inspecting the test material. Some of the motivation for the use of multiple sensing elements is to increase the spatial resolution of the material being characterized without loss of coverage, to add additional information for use in the estimation of multiple unknown material properties, and to cover large inspection areas in a faster time. These arrays can be used in both permanently mounted or scanning applications.

Figure 2:
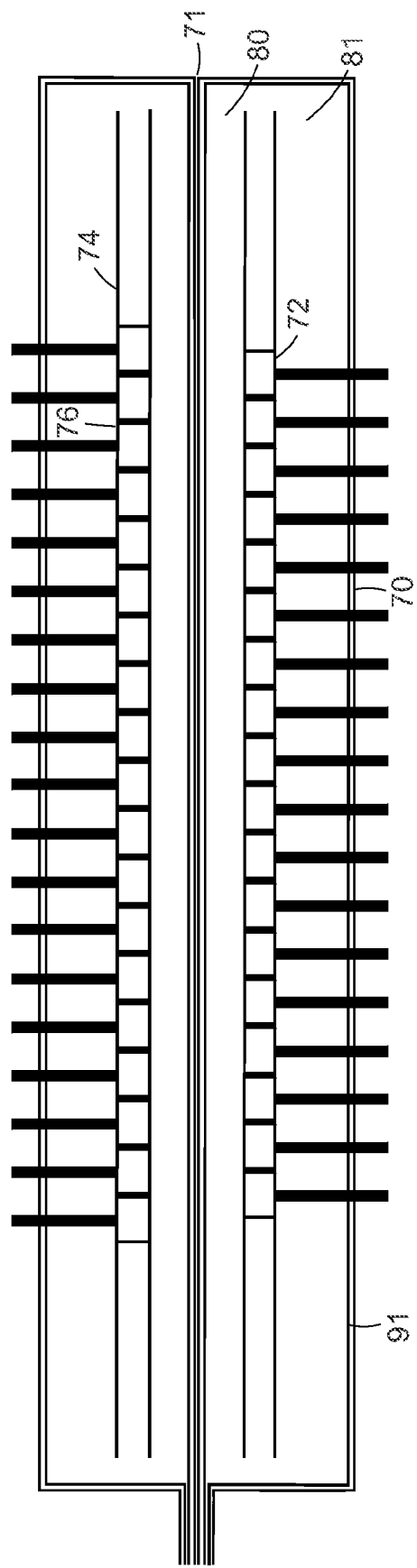
FIG. 2 shows a plan view of sensor array with a single primary winding and an array of sensing elements with connections to each individual element.
Figure 3:
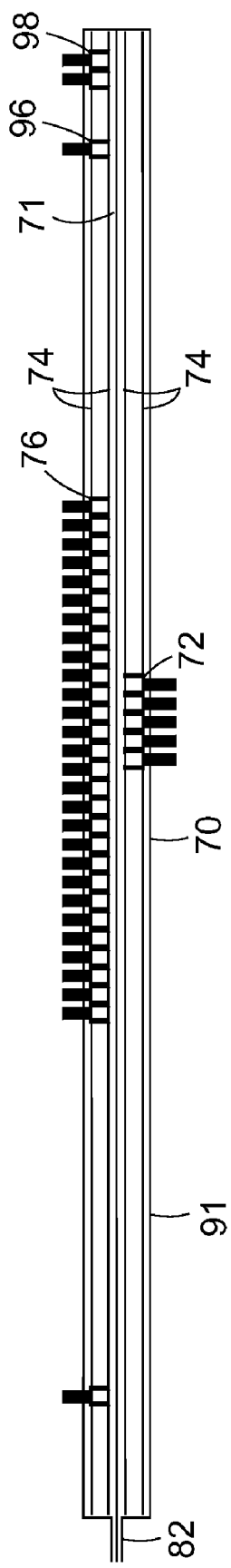
FIG. 3 is an expanded view of an eddy-current array where the locations of the sensing elements along the array are staggered.

The dimensions for the sensor array geometry and the placement of the sensing elements can be adjusted to improve sensitivity for a specific inspection. For example, the effective spatial wavelength or four times the distance 80 between the central conductors 71 and the sensing elements 72 can be altered to adjust the sensitivity of a measurement for a particular inspection. For the sensor array of FIG. 2, the distance 80 between the secondary elements 72 and the central conductors 71 is smaller than the distance 81 between the sensing elements 72 and the return conductor 91. An optimum response can be determined with models, empirically, or with some combination of the two. An example of a modified design is shown in FIG. 3. Here, most of the sensing elements 76 are located in a single row to provide the basic image of the material properties. A small number of sensing elements 72 are offset from this row to create a higher image resolution in a specific location.

Figure 4:
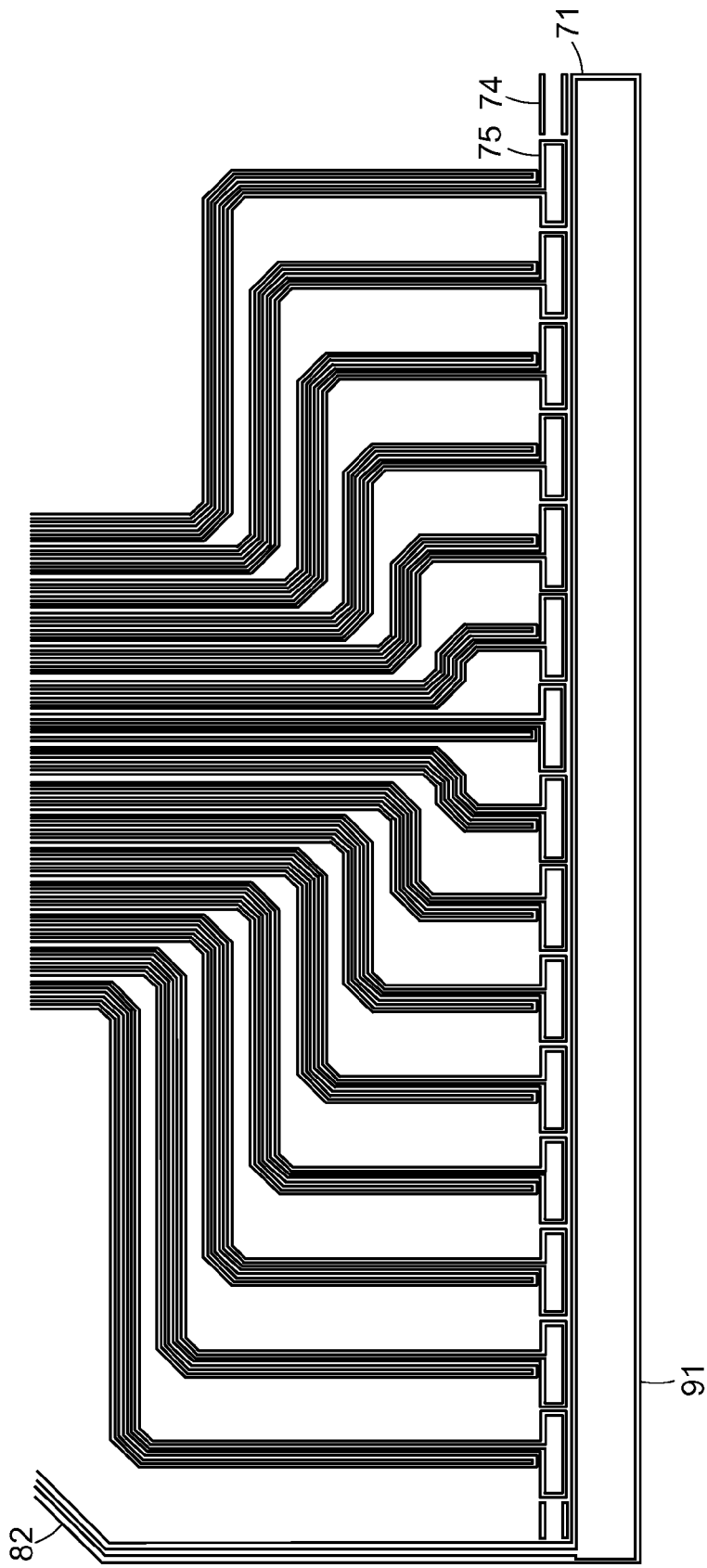
FIG. 4 is an expanded view of an eddy current array with a single rectangular loop drive winding and a linear row of sense elements on the outside of the extended portion of the loop.

The number of conductors used in the primary winding can be reduced further so that a single rectangular drive is used. As shown in FIG. 4, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. This distance can be optimized using models to maximize sensitivity to a feature of interest such as a buried crack or stress at a specific depth. Advantages of the design in FIG. 4 include a narrow drive and sense structure that allows measurements close to material edges and non-crossing conductor pathways so that a single layer design can be used with all of the conductors in the sensing region in the same plane. The width of the conductor 91 farthest from the sensing elements can be made wider in order to reduce any ohmic heating from large currents being driven through the drive winding.

An efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for near real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 5:
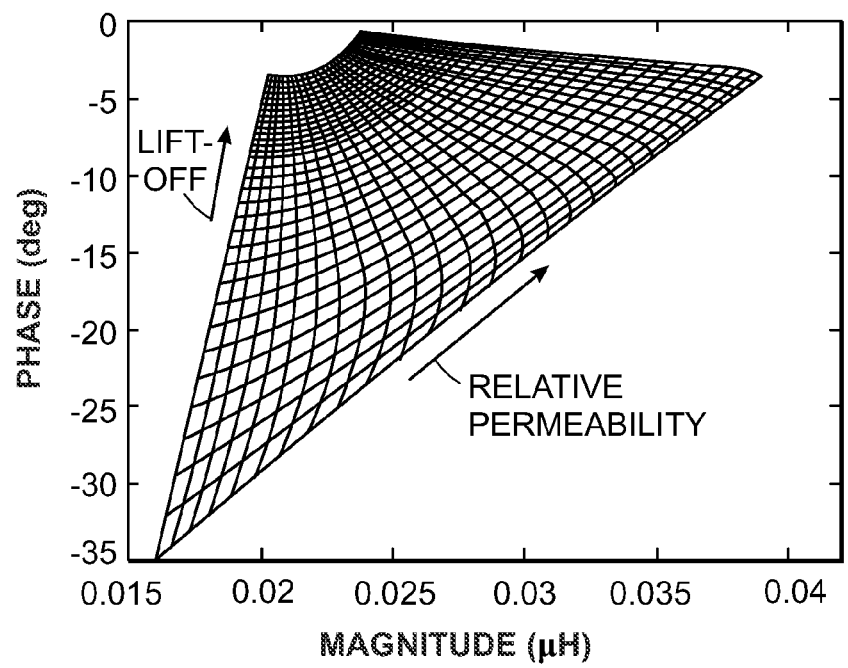
FIG. 5 shows a representative measurement grid relating the magnitude and phase of the sensor terminal impedance to the lift-off and magnetic permeability.
Figure 6:
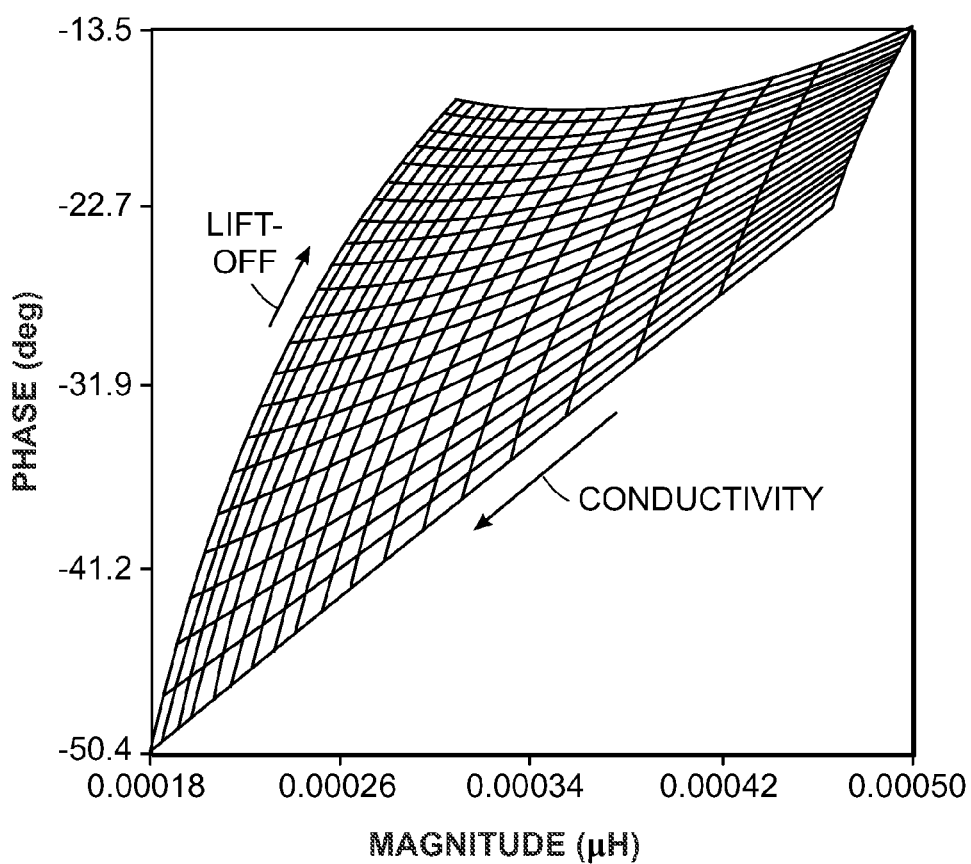
FIG. 6 shows a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 5. A representative measurement grid for a low-conductivity non-magnetic alloy (e.g., titanium alloys, some superalloys, and austenitic stainless steels) is illustrated in FIG. 6. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses. The effective property can also be a layer thickness, which is particularly suitable for coated systems. The effective property could also be some other estimated damage state, such as the dimension of a flaw or some indication of thermal damage for the material condition.

In addition to inductive coils, other types of sensing elements, such as Hall effect sensors, magnetoresistive sensors, SQUIDS, Barkhausen noise sensors, and giant magnetoresistive (GMR) devices, can also be used for the measurements. The use of GMR sensors for characterization of materials is described in more detail in U.S. patent application Ser. No. 10/045,650, filed Nov. 8, 2001, the entire teachings of which are incorporated herein by reference. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations.

Figures 7, 8:
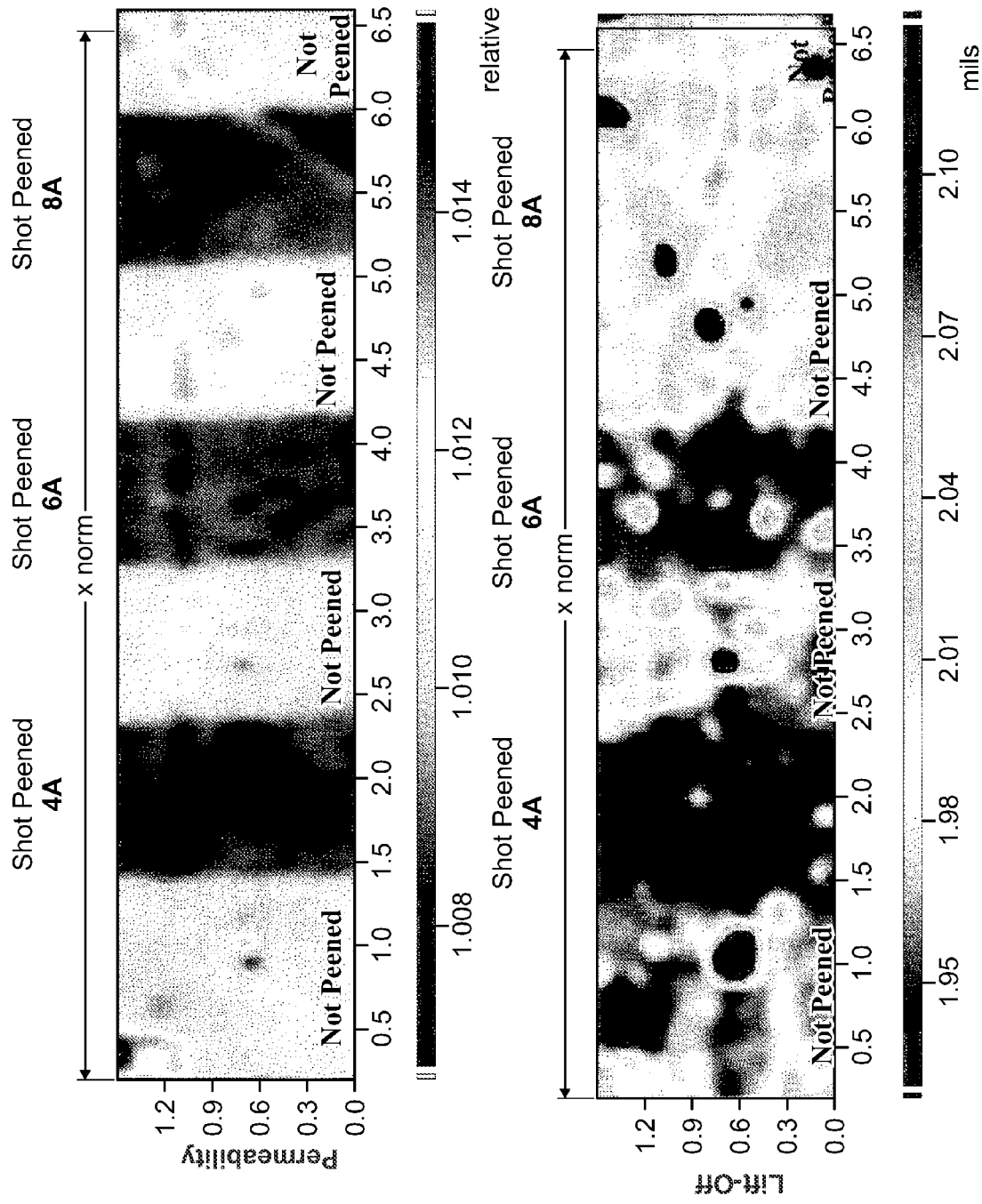
FIG. 7 shows a scanned image of the effective magnetic permeability for a shot peened IN-718 specimen.
FIG. 8 shows a scanned image of the effective life-off for a shot peened IN-718 specimen.

These sensors can be used to create high spatial resolution sensor responses of the effective material properties of materials before and after cold working. These responses can be in the form of one-dimensional plots of the sensor response with respect to the position or in the form of images of the response using position information in two-dimensions. This allows both local and global variations in the material to be observed and allows for compensation or suppression of the effects of the local variations. The cold working process can be in a variety of forms, such as shot peening, low plasticity or roll burnishing, or laser shock-peening. A representative scanned image of the effective magnetic permeability for a nickel superalloy component is shown in FIG. 7. This image was taken at an excitation frequency of 1 MHz and shows unpeened areas as well as areas peened to different intensities of 4, 6, and 8 Almens. The unpeened areas are distinct from the peened areas in the image, which indicates that these images can be used to indicate extent of coverage resulting from the peening process. But there are significant local inhomogeneities present as well. This also appears in the corresponding effective lift-off image of FIG. 8. The local inhomogeneities and variations in the material properties can lead to errors in the effective property measurements with large coil sensors that try to simply average out the background property variations. Indeed, the outliers can be significant enough to mask underlying correlations in the effective material property measurements with the cold working intensity. These high spatial resolution images allow the local outliers to be identified, and removed, so that the average material response without the outliers can be determined.

Figure 9:
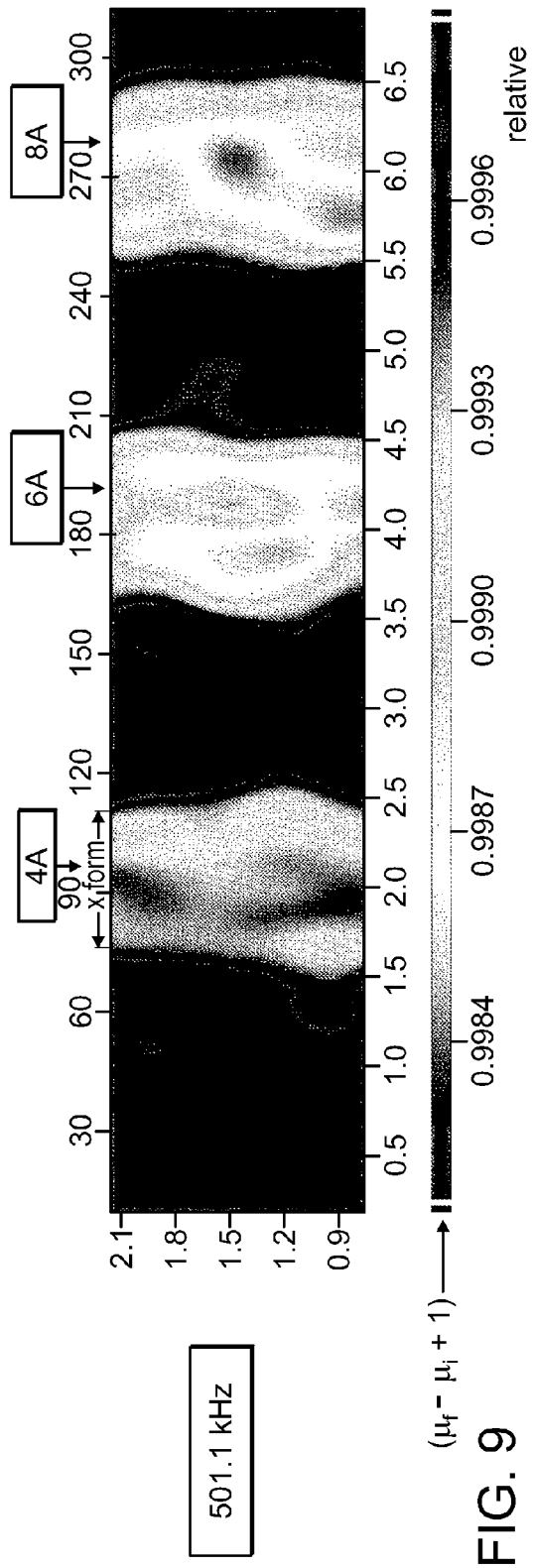
FIG. 9 shows an image of the difference in magnetic permeabilities at 500 kHz before and after the shot peening process.
Figure 10:
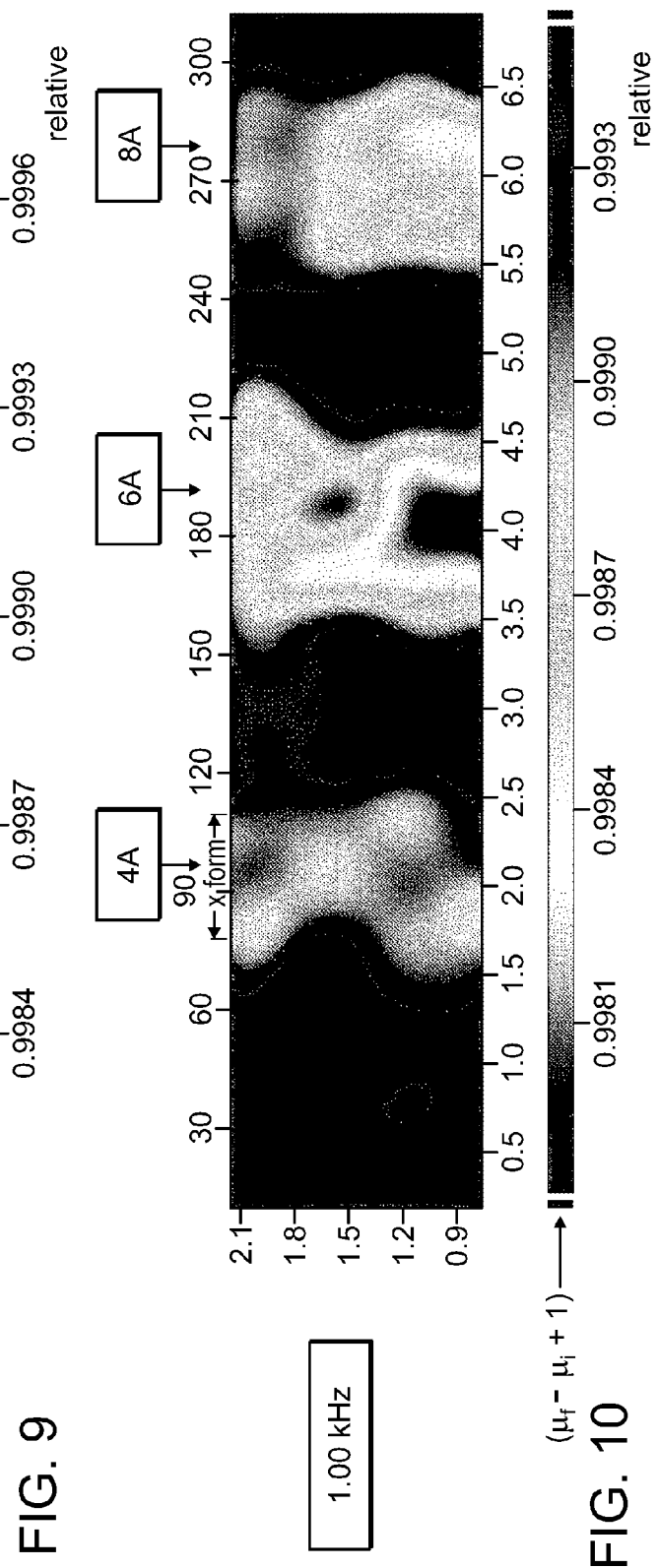
FIG. 10 shows an image of the difference in magnetic permeabilities at 1 MHz before and after the shot peening process.

One way to remove the effect of the background property variations and inhomogeneities in the material properties is to create spatially registered scan images of the material before and after the process is performed. The spatial registration is important because it ensures that any local response variations are aligned between any images. The difference between the data, and images, before and after the processing can then provide an indication of the shot peening or cold working intensity and extent. For example, FIG. 9 shows an image of the difference in the magnetic permeabilites (with an offset of 1 added) at an excitation frequency of 501.1 kHz. The corresponding image at 1 MHz is shown in FIG. 10. These images indicate that the baseline measurement prior to process can be combined with the post-processing data to provide information about the process itself. The variations in these properties can be correlated with other scales for the cold working process, such as the Almen intensity for a shot peening process. The multiple frequency data can also be combined to create a single image or set of data.

These example images were for a nickel-based superalloy material. Similar measurements can be performed on other materials, such as aluminum alloys. Furthermore, the measurement images and data do not have to be converted into effective material properties. The same processing can be applied to the raw sensor responses. Note also that these measurements can be performed with flexible sensors that can conform to the surface geometry of complex sample shapes. This allows the measurements to accommodate a variety of curved parts, including engine blades, disk slots, bores, and webs.

For eddy current sensors, the induced eddy currents in a conducting material tend to follow the path of the conducting drive winding segments. For the sensors described above which have at least one linear conducting segment, this provides a preferential orientation for the currents induced in the test material and also permits the measurement of anisotropic or directional-dependent material properties. This capability for anisotropic property measurements can be used to assess the material condition and quality of an operation. While most materials have isotropic properties, such as the electrical conductivity, in others anisotropy can be introduced by a preconditioning operation. This preconditioning operation is performed prior to a process or in-service exposure so that any changes in the anisotropy of the material properties can be used to determine the quality or severity of the process or exposure.

Figure 31:
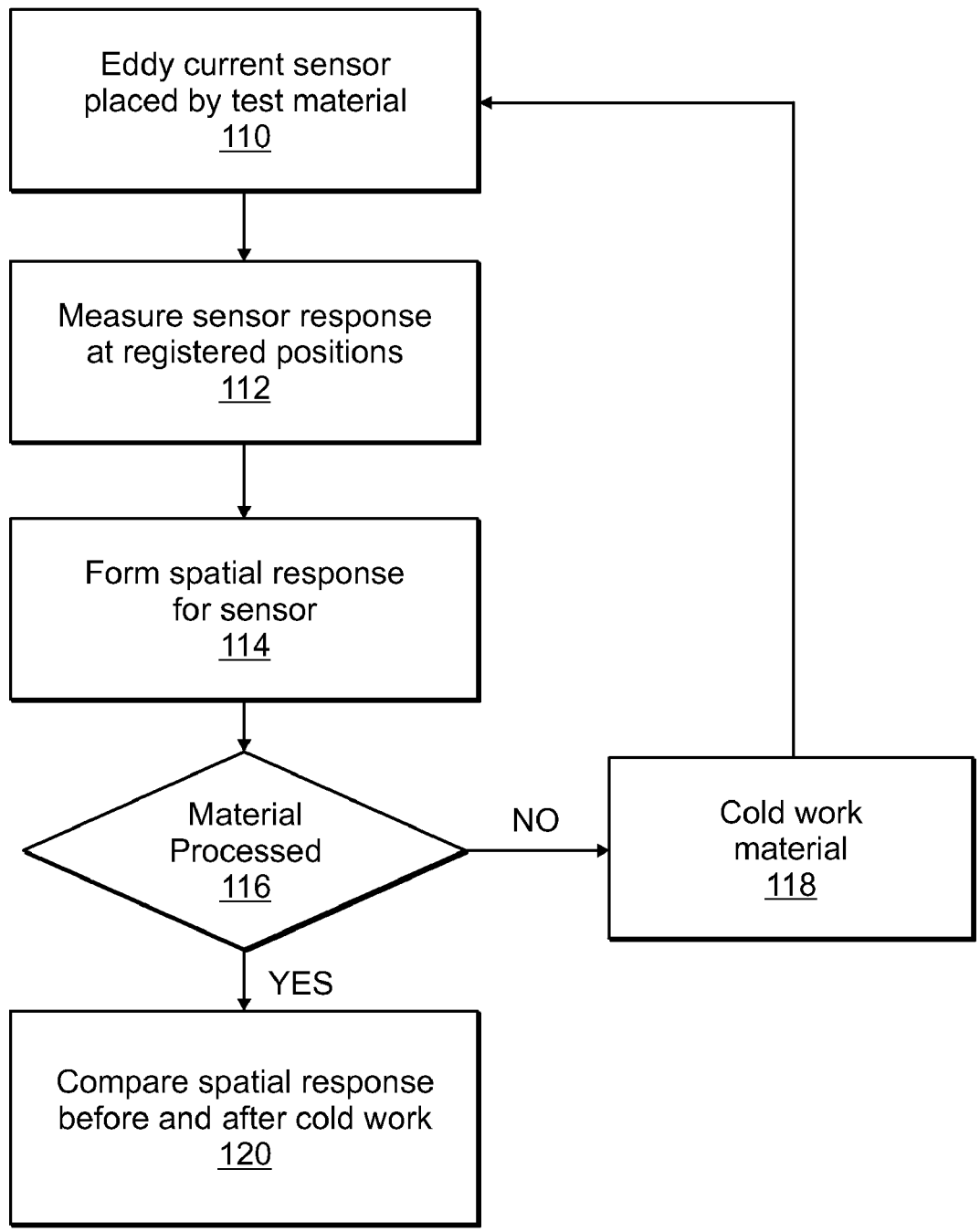
FIG. 31 shows a flow diagram for the use of registered spatial responses.

FIG. 31 shows a flow diagram for the cold work process quality assessment using registered spatial responses taken before and after a cold work process. First an eddy current sensor or sensor array is placed near the test material (110). The sensor response is then measured as the sensor is scanned over the surface of the test material (112). The sensor response, in one or two spatial dimensions, is then combined with position information to create a spatial response (114). If the material has not been cold worked (116) then the material is cold worked (118) and the measurement process repeated. Typically the sensor is removed or moved aside so that the material can be processed and the sensor does not affect the cold working process. After processing and the additional measurements are performed, the spatial responses taken before and after the cold working are compared (120) and used to assess the quality of the cold working process.

Figure 11:
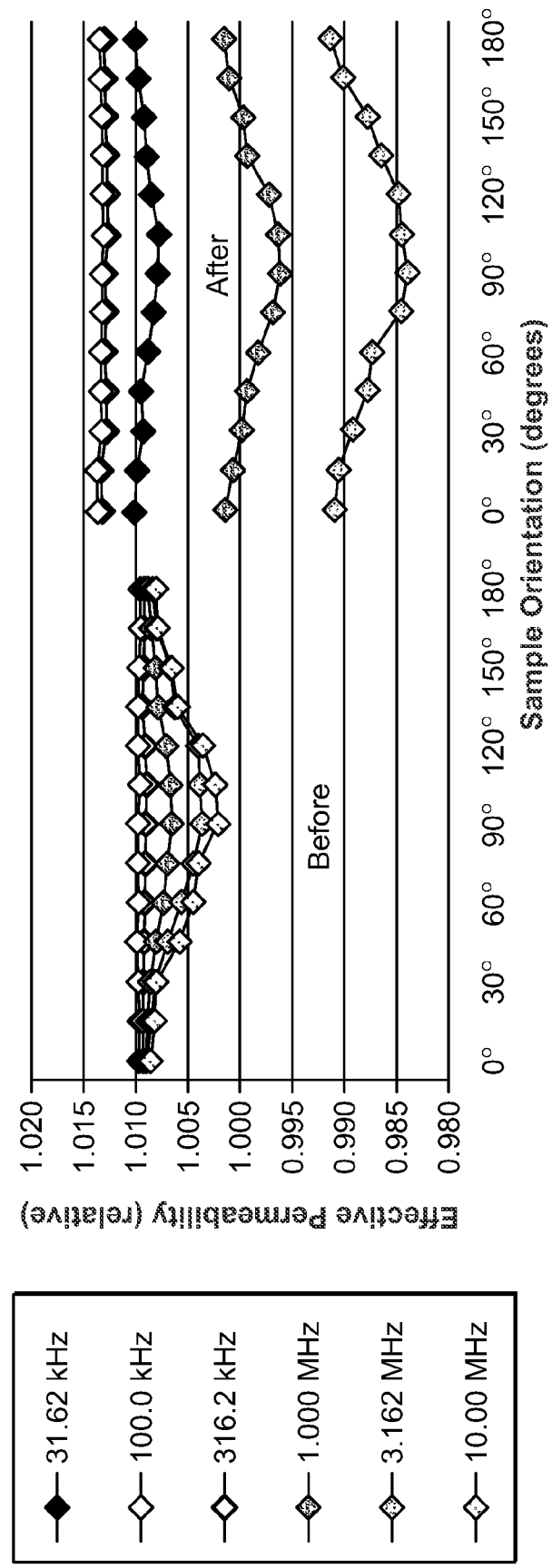
FIG. 11 shows a multiple frequency plot of the effective magnetic permeability for an IN-718 alloy before and after a low temperature thermal treatment.
Figure 12:
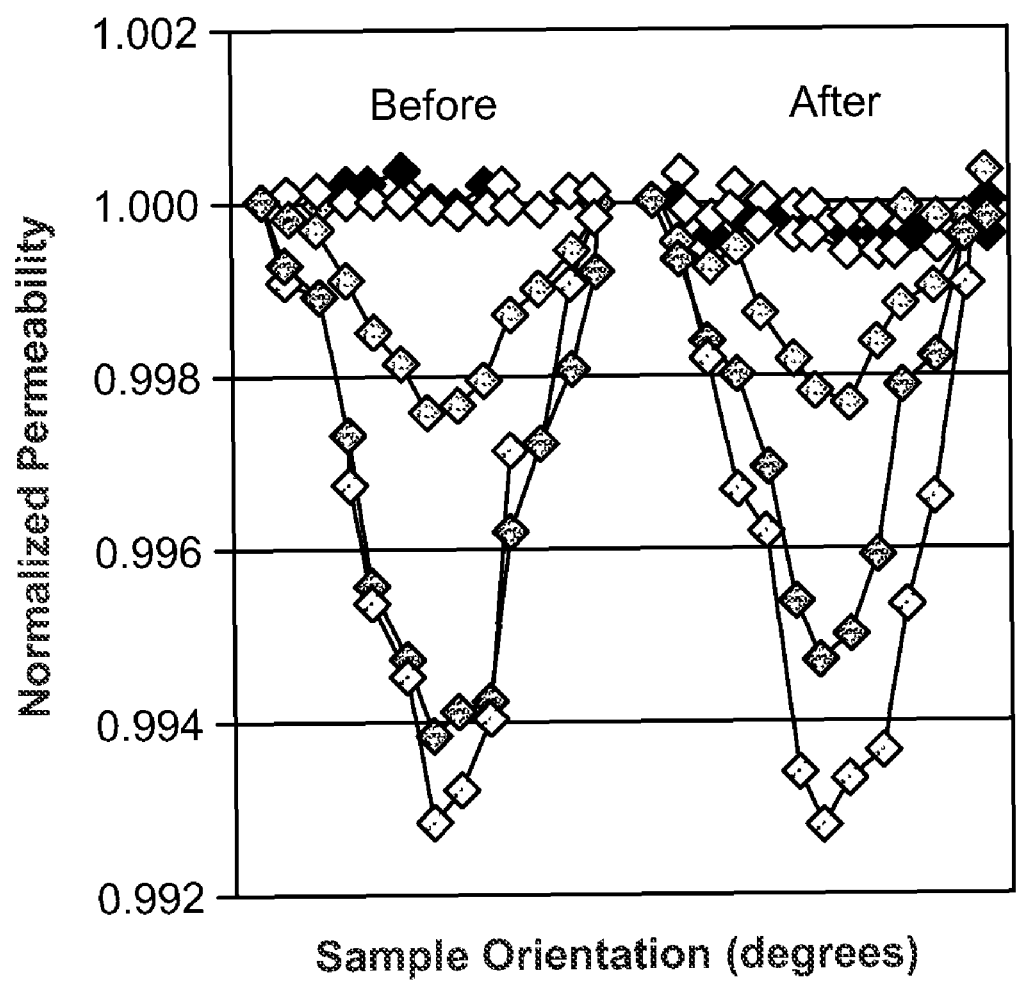
FIG. 12 shows a normalized plot of the effective magnetic permeability for an IN-718 alloy before and after a low temperature thermal treatment.
Figure 13:
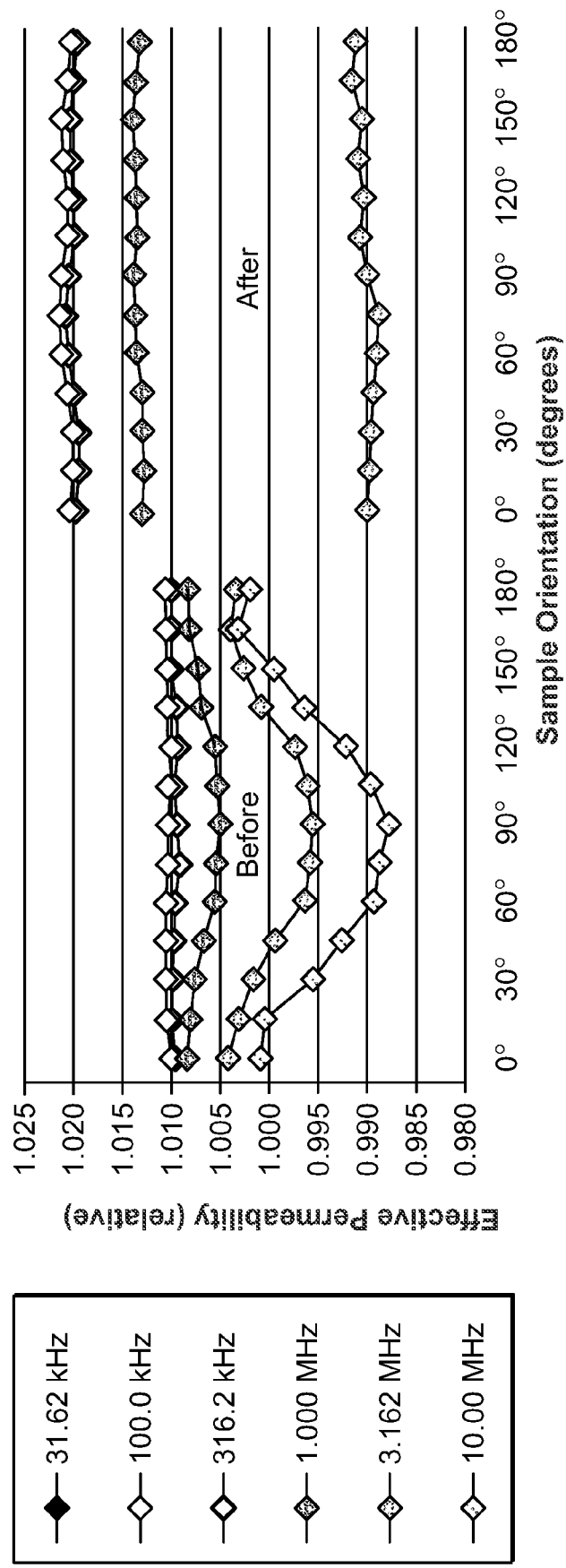
FIG. 13 shows a multiple frequency plot of the effective magnetic permeability for an IN-718 alloy before and after a high temperature thermal treatment.
Figure 14:
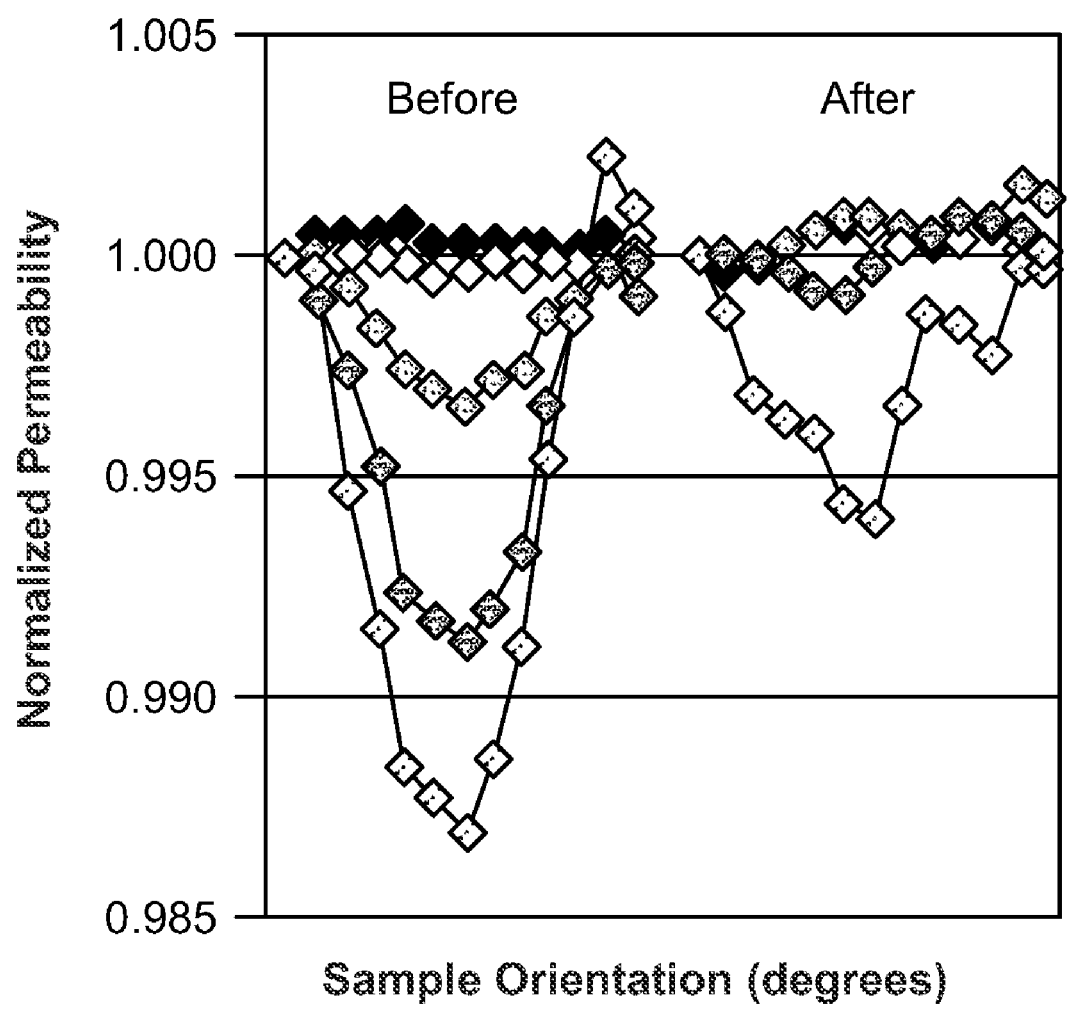
FIG. 14 shows a normalized plot of the effective magnetic permeability for an IN-718 alloy before and after a high temperature thermal treatment.

As an example, FIG. 11 shows a plot of the effective magnetic permeability at several excitation frequencies for a shot peened IN-718 (nickel superalloy) as the sensor or sample orientation is varied. In this case, there is a measurable anisotropy in the material as the permeability at the 90° orientation is lower than the permeability at the 0° orientation. This is shown more clearly in the normalized plot of FIG. 12 where the data at each frequency was normalized by the 0° data. This sample underwent a thermal heat treatment of 600° C. for 24 hours. After the heat treatment, there is a significant change in the permeability of the material, particularly at the lower frequencies, which is consistent with the relaxation of the residual stresses introduced during the shot peen process. However, since the anisotropy has not changed appreciably, the heat treatment was insufficient for microstructural changes in the material. Similarly, FIG. 13 shows the multiple frequency and orientation data for another shotpeened IN-718 sample. In this case, the sample underwent a thermal heat treatment of 650° C. for 48 hours, which was sufficient for both stress relaxation and microstructurally changing or aging of the material. The microstructural change is apparent in the lack of anisotropy in the magnetic permeability after the heat treatment, as illustrated in the normalized plot of FIG. 14.

Figure 15:
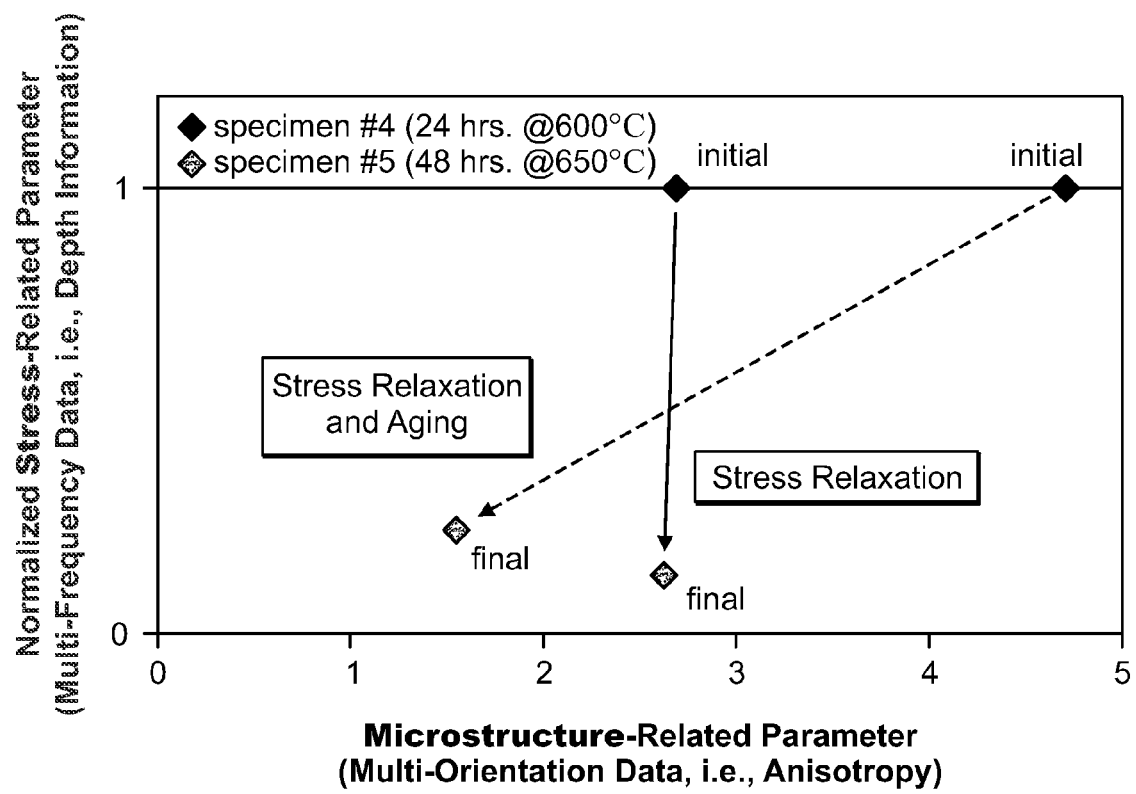
FIG. 15 shows a plot comparing stress-related information to the thermal treatment condition for an IN-718 alloy.

The ability to separate the stress relaxation effects from the combination of stress relaxation with microstructural changes is illustrated in FIG. 15. The normalized stress-related parameter reflects the multiple frequency data and the depth information for the residual stress caused by the shot peening process. The microstructure-related parameter reflects the anisotropy or multiple orientation data. The baseline data, obtained prior to the heat treatment, indicates that the initial stress level was the same for both samples. The usage and damage state data taken after the heat treatment does not change very much for the low temperature treatment but significantly changes for the higher temperature treatment.

The above example illustrated the approach for monitoring a material condition, such as the usage or thermal history of a material, by using anisotropy of an electrical property measurement. Similarly, this approach can be used to assess the quality of a process. For example, the preconditioning action could be a mechanical overload situation that introduces an anisotropic electrical property. The process could be a shot peening operation on a material such as titanium. The variation in the anisotropy in this case can reflect the quality of the peening process.

As part of this assessment of the process quality, it may be desirable to correct or compensate for the effects of surface roughness variations in the sample. An algorithm for compensating for the surface roughness for shot peening, as described below, can also be applied to other cold working process. It involves converting the sensor response data into effective properties. While numerical or other methods may also be used, it is preferable to use measurement grids to convert the measurement data into effective properties and also to calculate the sensor responses given the material property values of interest. For this algorithm, the inputs are a weighting factor a and a peak-to-valley height for the surface roughness $h_s$. The following steps can be followed:

1. Obtain eddy current sensor responses for at least two excitation frequencies on both an unpeened material and a peened material. Convert these sensor responses into effective lift-offs (h) and conductivities and normalize the responses with respect to the reference responses by $$\sigma_l = \sigma_{ref}(\sigma_{ml}/\sigma_{rl})$$

$$\sigma_h = \sigma_{ref}(\sigma_{mh}/\sigma_{rh})$$

with σ the electrical conductivity, l denoting a low frequency, h denoting a high frequency, m denoting a measurement on the unknown property sample, r denoting the measured values on the reference sample, and ref denoting the reference value for the reference sample. The low frequency is typically chosen so that it penetrates through the compressive surface layer created by the peening process and the high frequency is typically chosen to reflect the properties of the surface layer itself.

2. Determine the expected impedance (Z) at low ($Z_l$) and high ($Z_h$) frequencies using the normalized high frequency conductivity ($\sigma_h$) for both and a range of lift-offs. The lift-offs range from −1 µm to a maximum $h_s$ (typically 25-50 µm) in addition to the measured reference sample lift-off at each frequency. The negative value for the lower bound assures that lift-off noise will not cause numerical instabilities with the algorithm.

3 For each $h_s$ value an estimate for the measurement response for both frequencies is obtained from $$Z_{mi} = \alpha^2 Z_i(\sigma_h, h_i) + (1-\alpha^2) Z_i(\sigma_h, h_i + h_s)$$

where the subscript i denotes either the low or the high frequency responses.

4. These estimated measurement responses are then converted into effective conductivities ($\sigma_{eff,i}$) and lift-offs ($h_{eff,i}$) for each frequency.

5. These lift-offs are then used to determine the $h_s$ value for each frequency which minimizes the error between this effective lift-off and the lift-off obtained with the unknown sample. This lift-off is then also used to determine the effective conductivity.

6. Determine the frequency ratio that can be correlated with the shot peen intensity. This can be expressed as $$R = \frac{\sigma_h}{\sigma_l} \frac{\sigma_{eff,l}}{\sigma_{eff,h}}$$

Figure 32:
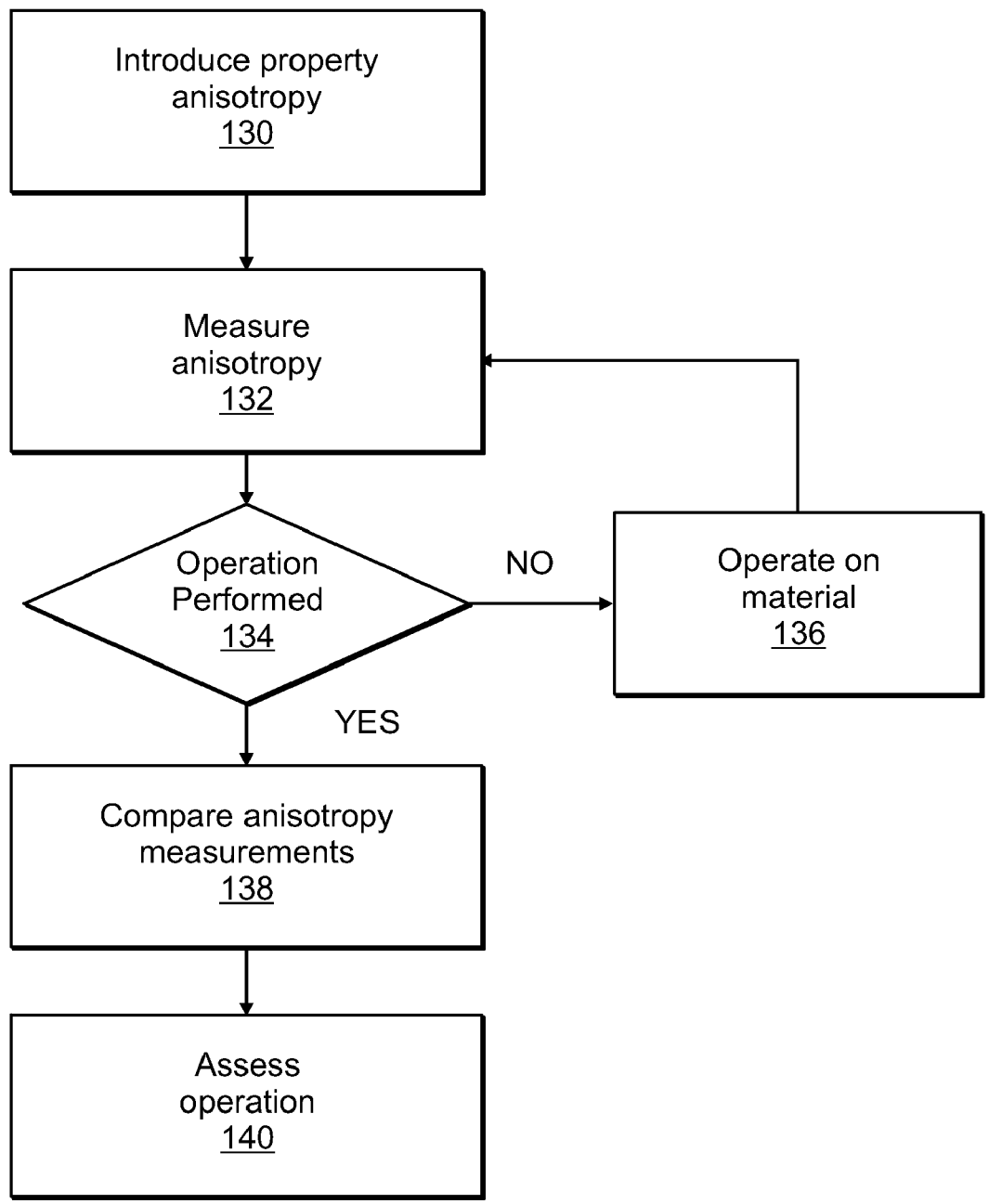
FIG. 32 shows a flow diagram for the use of anistropic property measurements to assess material condition or operation quality.

FIG. 32 shows a flow diagram for the use of anisotropic or directionally dependent material properties to assess a material condition or the quality of an operation. First, anisotropy is introduced into the test material (130). This may occur naturally or may be the result of a preconditioning action, such as mechanical overload applied to test material that results in plastic deformation. The anisotropy is then measured (132) with a sensor that can provide direction-dependent property values. An operation is then performed on the test material (136) and the anisotropy in the property is measured again. This operation may be a discrete event, such as shot peening, or it may be a change in material condition with time due to environmental or service-related exposure. If the operation has been performed on the material (134), then the anisotropy measurements taken before and after the exposure (or at different time periods) are compared (138) and used to assess the operation (140). This assessment may simply be to determine if the anisotropy changed or could be used to quantitatively determine the intensity of the operation.

Figure 16:
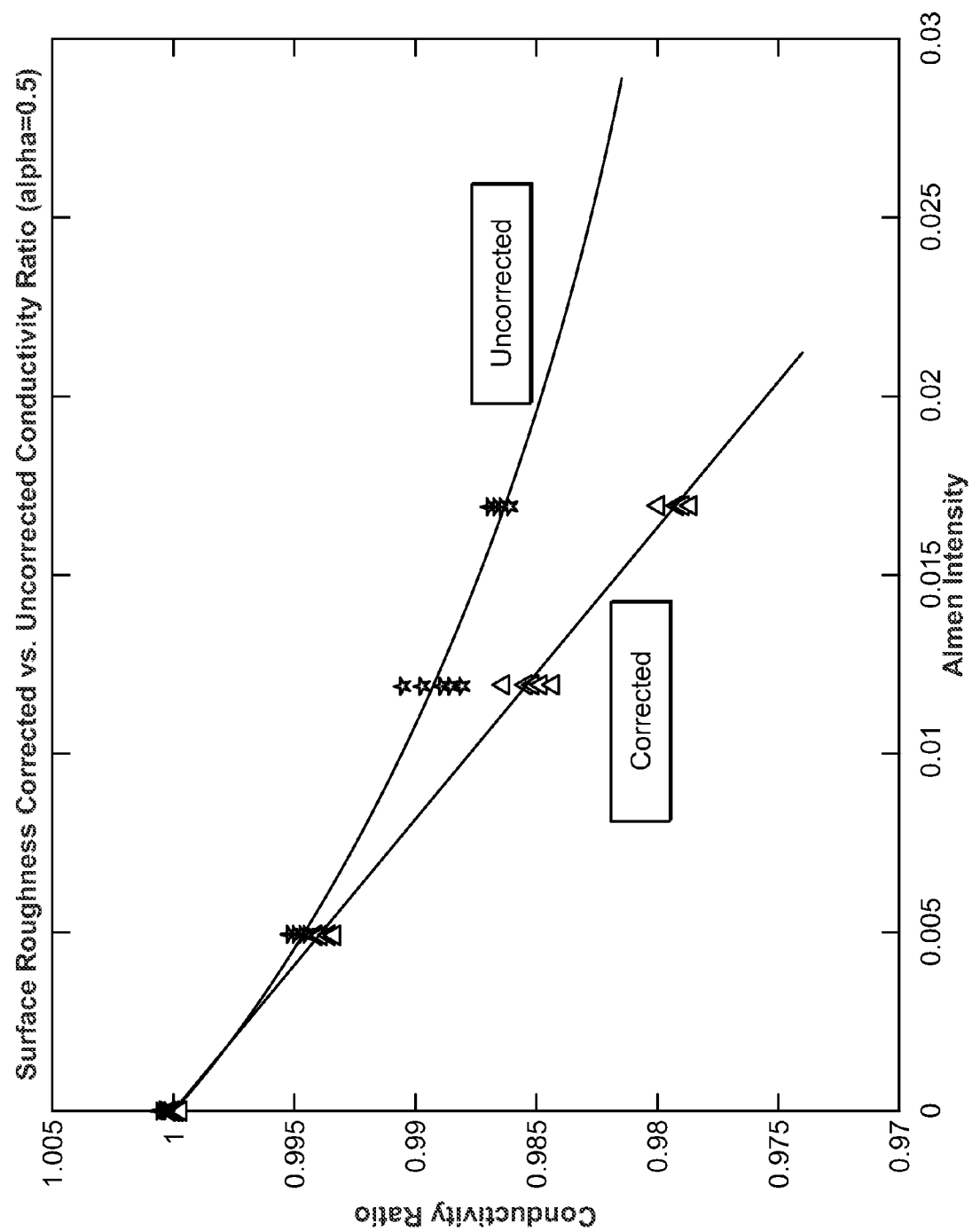
FIG. 16 shows a plot of the high-to-low frequency conductivity ratio versus Almen intensity both with and without a correction for surface roughness.

The effect of correcting for the effect of the surface roughness is plotted in FIG. 16. In this case, the roughness correction compensates for the non-linear response so that the corrected conductivity ratio varies linearly with Almen intensity. This makes the corrected conductivity ratio more suitable for use in process controllers that typically rely on linear sensor responses. Furthermore, once suitable parameters are found for the surface correction, the measurements grids can be corrected as well so that the databases of responses can more directly provide the estimates of the corrected conductivities for the conductivity ratio.

Figure 17:
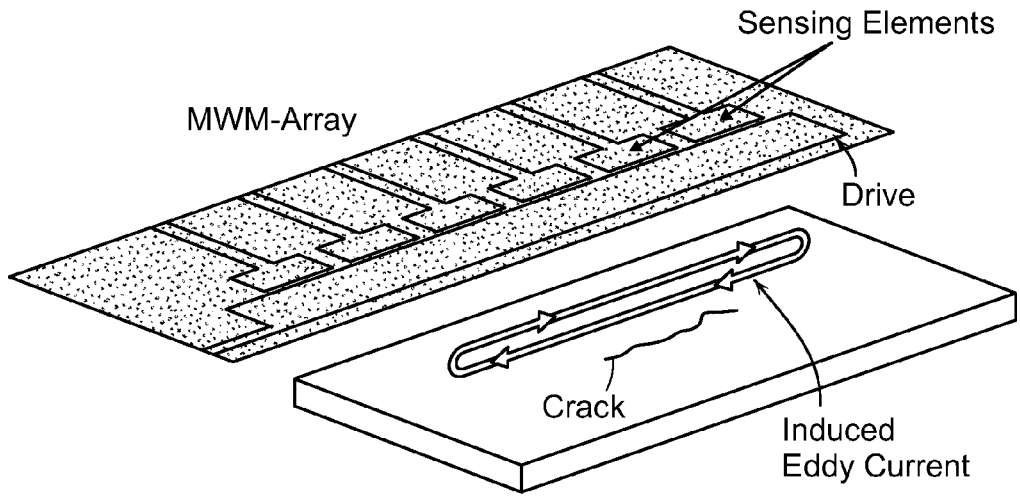
FIG. 17 shows a sensor winding with a linear conducting drive segment parallel to the crack orientation.
Figure 18:
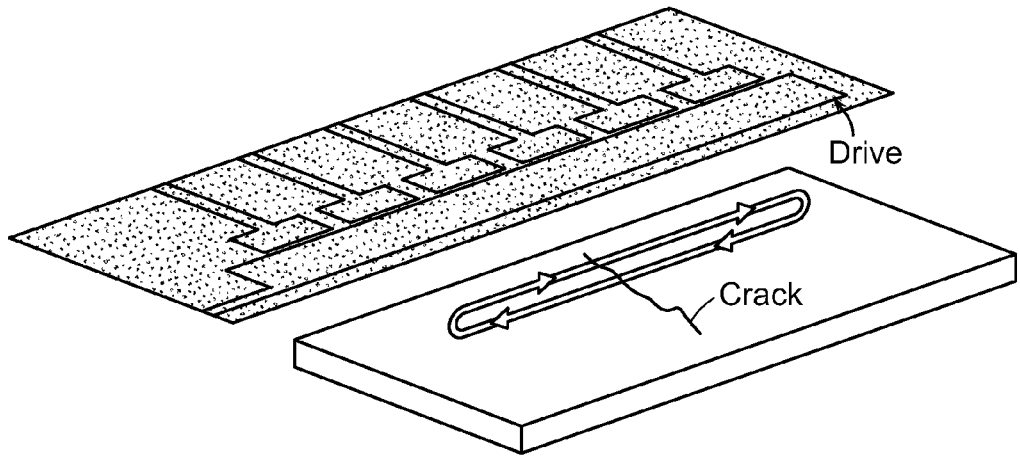
FIG. 18 shows a sensor winding with a linear conducting drive segment perpendicular to the crack orientation.
Figure 19:
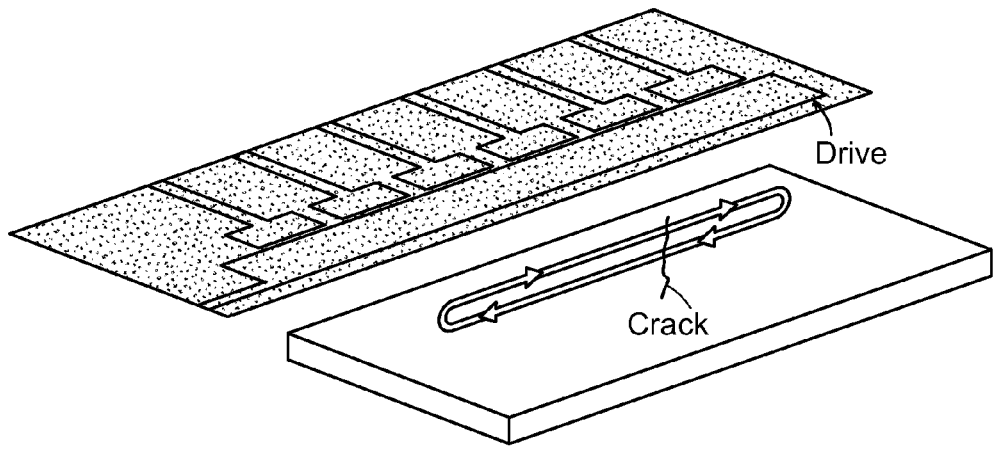
FIG. 19 shows a sensor winding with a linear conducting drive segment at an angle to the crack orientation.
Figure 20:
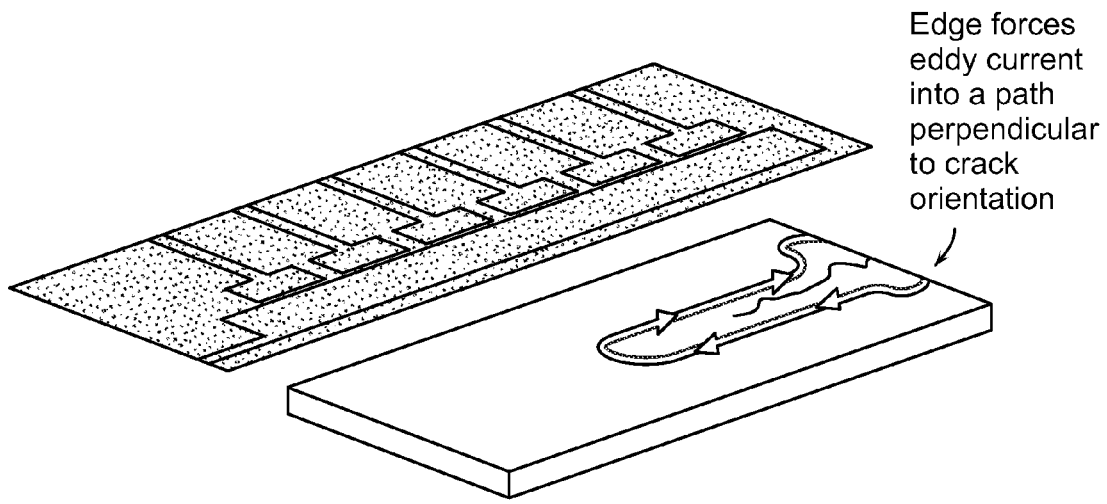
FIG. 20 shows a sensor winding with a linear conducting drive segment parallel to the crack orientation with the crack at an edge of the material.

As mentioned above, the MWM-Array sensors have a linear drive conductor near the sensing elements, which creates induced eddy currents in the material that are predominantly along one axis. Cracks will alter the flow of eddy currents within the material, and the orientation of the drive with respect to the crack affects how the eddy currents are altered by the crack. Though the sensors are sensitive to the presence of cracks in all orientations as shown in FIG. 17, the greatest sensitivity, for cracks away from material, such engine slot, edges, is achieved when the drive is perpendicular to the crack orientation, as shown in FIG. 18. However, scanning across a crack, instead of along the crack, is preferred, since higher data resolution is possible in the scan direction. This makes 45° relative drive/crack orientations useful for high sensitivity and high resolution, as shown in FIG. 19. High sensitivity can also be achieved for cracks at edges when the drive is parallel to the crack because the presence of the edge forces the eddy currents to loop back, as shown in FIG. 20. This results in a concentration of eddy currents along the edge in the direction perpendicular to the crack orientation, as required for maximum detection sensitivity.

Figure 21:
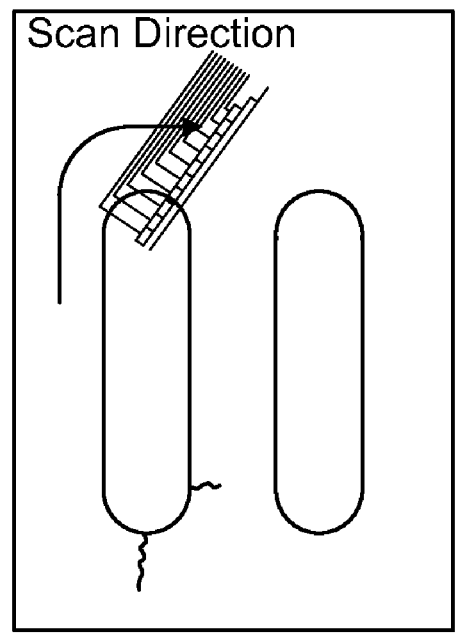
FIG. 21 shows a contour scan option with a linear conducting drive segment of a sensor array perpendicular to the material edge.
Figure 22:
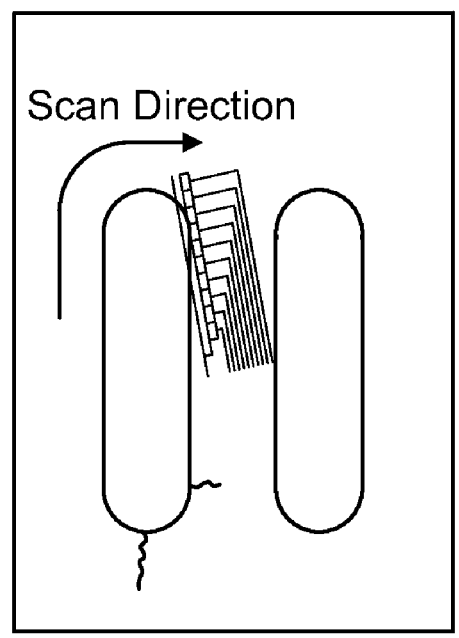
FIG. 22 shows a contour scan option with a linear conducting drive segment of a sensor array parallel to the material edge.

When inspecting the real articles, there are a number of ways the sensor can be scanned across the slots in materials to image property values in the material. The most rapid is a circumferential scan path, where the sensor is scanned across multiple slots in one motion. A second scan path is axial, where the sensor is scanned in the direction of the slot axis. Depending on sensor width, one or two slots could be inspected with each scan stroke. In either of these two scan paths, the drive can be either perpendicular to or angled with respect to the scan direction. A third method is a contour scan path, which provides the highest sensitivity to cracks. For this path the sensor is traversed and rotated during the scan of a slot so that the drive maintains the same orientation with respect to the edge, and the same sense element is traversed around the edge. Methods for performing a contour scan are shown in FIG. 21 and FIG. 22.

Figure 23:
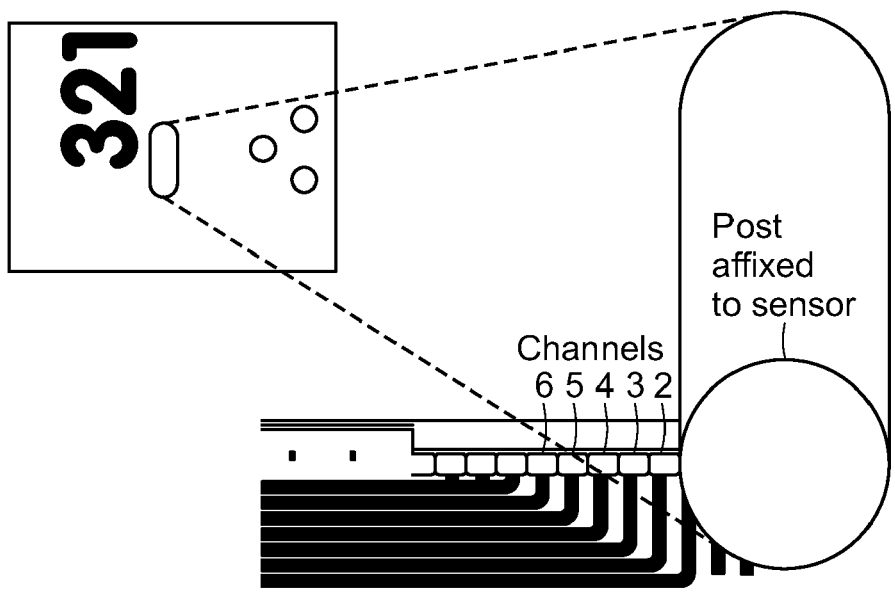
FIG. 23 shows a shallow post placed in the slot and attached to the sensor array to facilitate maintaining sensor array orientation as the sensor array is scanned around the contour of the slot.

A limitation of the current contour scan methods is that the sense element position must be kept nearly constant with respect to the edge of the slot throughout the scan. The contour scan path was demonstrated by affixing a flexible sensor array to a post that slipped into the slot, as shown in FIG. 23. 180° manual scans around the apex of the slot were then performed, and the post assured that the sense element position from the edge of the slot was held constant through the duration of the scan. While sensitivity is lost if the sensor deviates too much from its optimum distance from the edge, model based methods permit a significant relaxation of this requirement, by correcting for such edge position variations. This correction for has been described in U.S. patent application Ser. No. 11/249,047 filed Oct. 11, 2005, the entire teachings of which are incorporated herein by reference, as a signature library approach.

Figure 24:
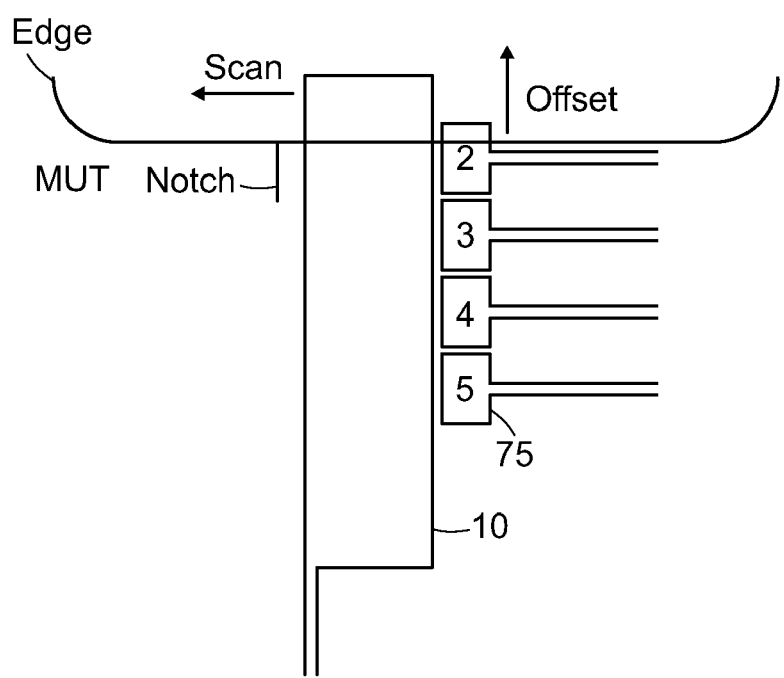
FIG. 24 shows a schematic diagram of an MWM scanned over an edge of a test material.
Figure 25:
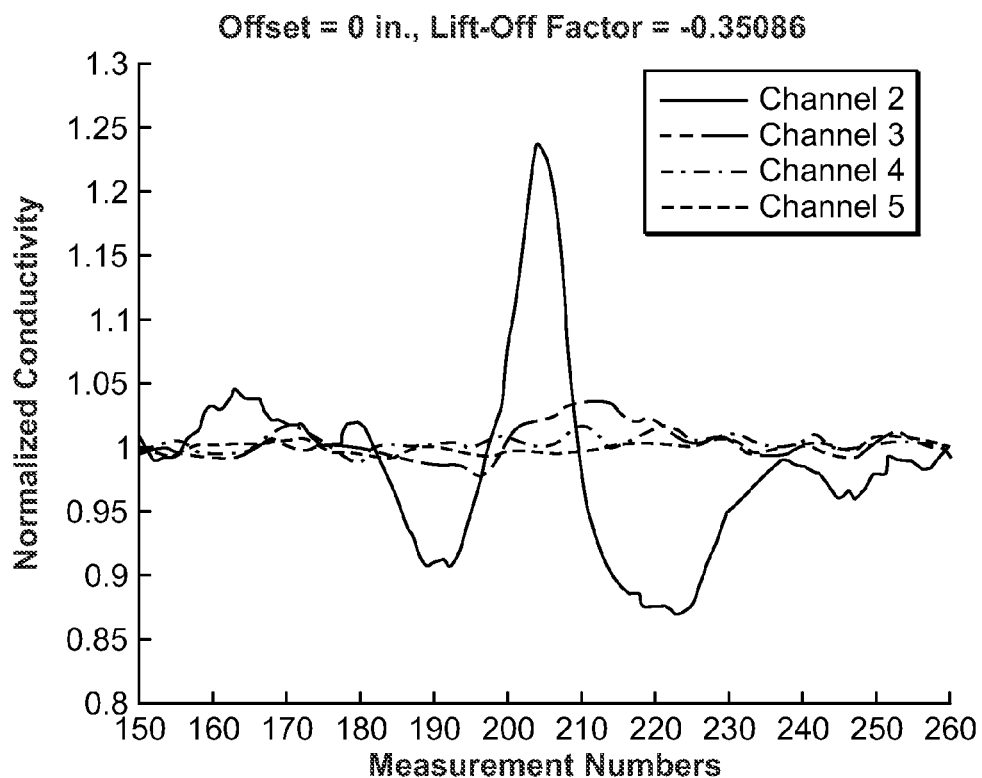
Figure 26:
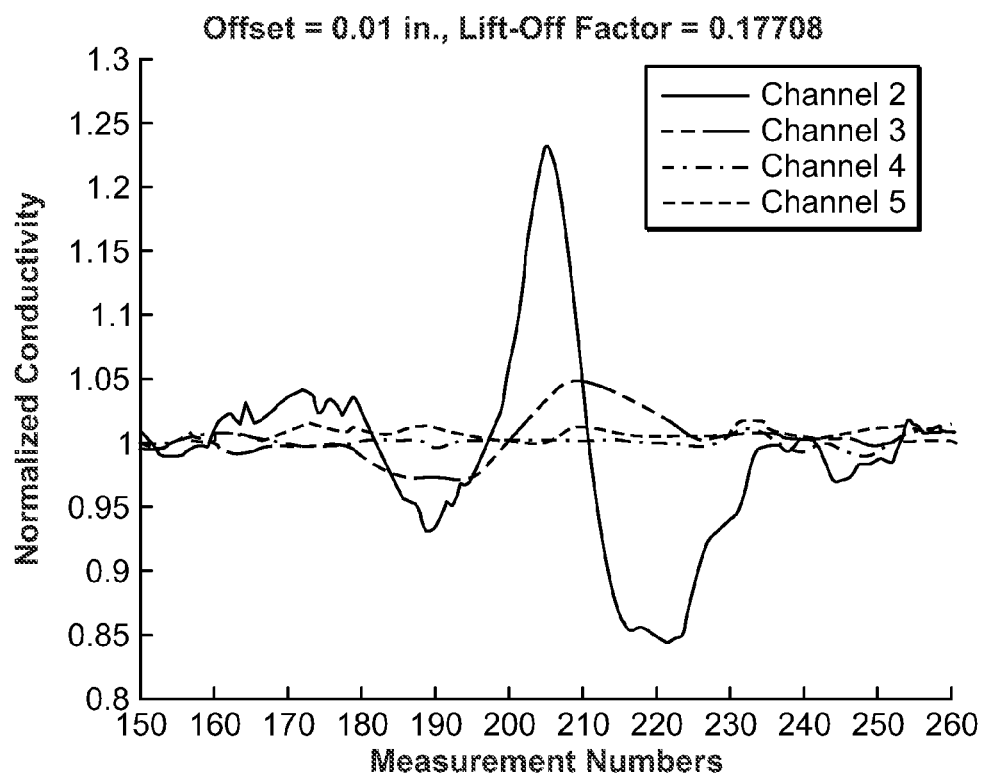
Figure 27:
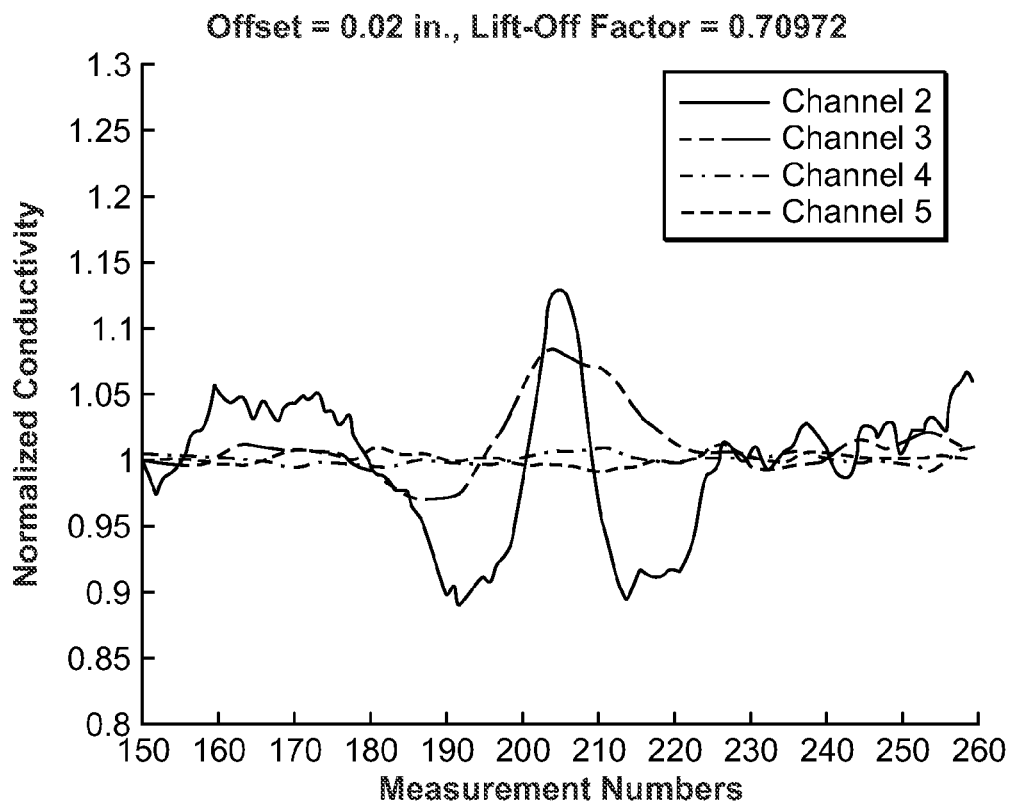
Figure 28:
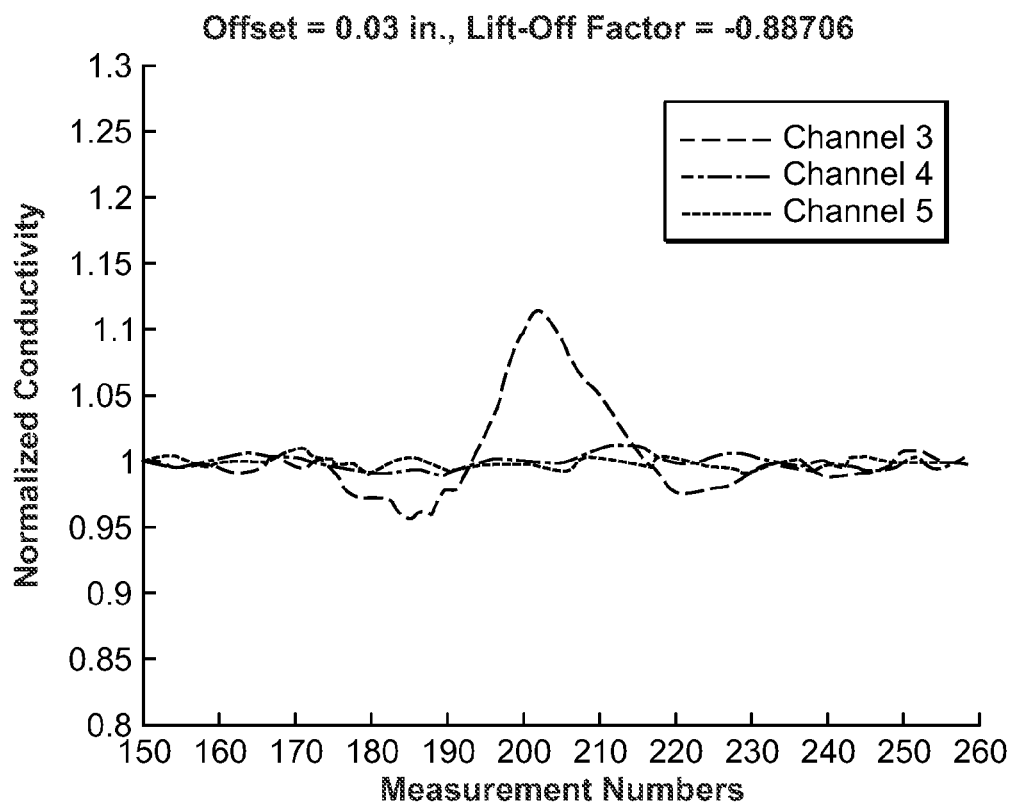
Figure 29:
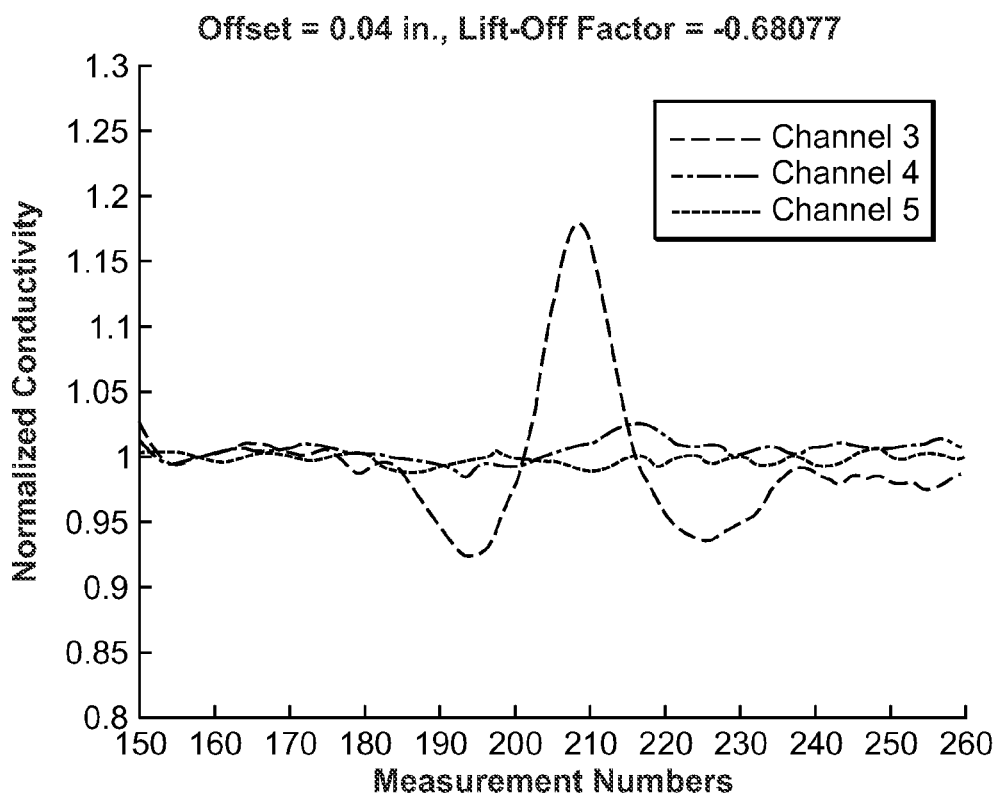
Figure 30:
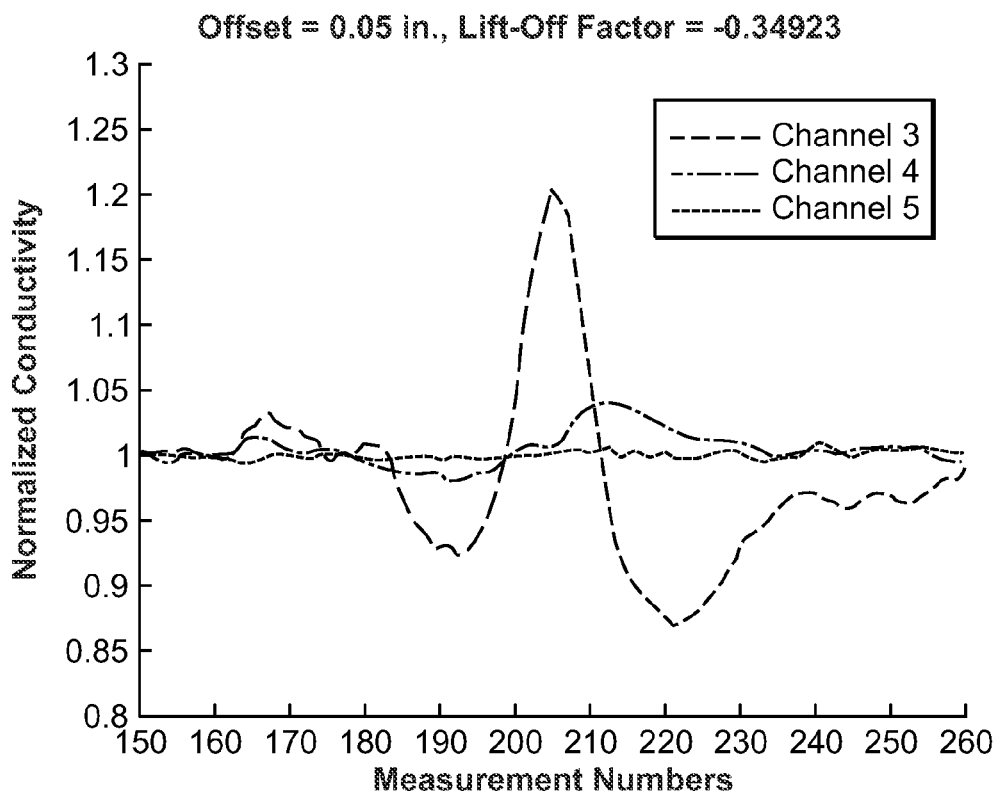

One such example implementation of a signature library is shown in FIG. 24, where a crack is at the edge of the MUT. As the sensor array is scanned along the edge, any misalignment or offset of the sense elements with respect to the edge can change the signature response to the crack (or notch) and limit the sensitivity of the measurement. FIGS. 25-30 show the results of repeatedly scanning a sensor array along the edge of a flat specimen with various offset distances of the sensor array from the edge. Note that the channel numbers in these plots correspond to the sense elements shown in FIG. 24 and the distance between sense element centers is about 0.050 in. In FIG. 25, the offset distance is 0.0 in. and channel 2 is approximately centered over the edge of the test material. As the offset distance increases to 0.01 in. (FIG. 26) and 0.02 in. (FIG. 27), the shape of the crack response changes dramatically. When the offset distance has increased to 0.03 in. (FIG. 28) channel 2 is off of the test material and channel 3 is at the edge of the material. Increasing the offset distance further now causes the crack response curve to change for channel 3. When the offset distance is 0.05 in. (FIG. 30) channel 3 is centered over the edge of the material and the crack response is similar to that of channel 2 when the offset distance was 0.0 in. (FIG. 25). This self-similarity of the sense element responses indicates that if the relative position of the sense element or channel from the edge could be determined, then the correct signature could be selected for filtering of the crack response data.

The appropriate signature scan for filtering the response data is determined through a lift-off factor. The lift-off factor is a linear function of the mean effective lift-off h in a short section of the scan preceding the EDM-notch response and defined by $$\text{lift-off factor} = \frac{h - h_o}{a}$$

The constant $h_o$ is chosen so that the lift-off factor is zero for the position of the sensing element relative to the edge that produces the largest EDM-notch response. The constant $\alpha$ is chosen so that the lift-off factor varies from approximately −1 to 1 over the range of positions of a sensing element relative to the edge for which it is the member of the array most sensitive to the EDM-notch. Note that a lift-off factor can be calculated for each sensing element independently. In FIGS. 25-30, the lift-off factor given corresponds to the sensing element which is most sensitive to the EDM-notch.

Note that the procedure for determining the lift-off factor involved performing a series of scans over a notch along the edge of a test material. These scan responses, as a function of position along the edge, are stored as crack signatures. This signature response library can then accessed when an inspection is performed on a test material that is part of or from a component, so that measurements on test parts could use the lift-off factor to determine the appropriate reference scan for filtering of the data. The shape filtering of data is described, for example, in U.S. Pat. No. 6,784,662 and U.S. patent application Ser. No. 10/345,883, filed Jan. 15, 2003 and Ser. No. 11/229,844, filed Sep. 19, 2005, the entire contents of which are incorporated herein by reference. This filtering allows the measurement data to be compared to the reference response to highlight the presence of a crack. Note that the signature responses can be determined empirically or through numerical methods. Furthermore interpolation between reference scans can be used to create the final reference scan compared to the measurement data. This lift-off factor can also be used to correct the response of adjacent sense elements in a sensor array. For example, this reference parameter could be used to select the appropriate response signature for the adjacent element, assuming a notch or crack at the edge, which should provide complementary information about any indicated flaws and may help to reduce the false call rate.

While the inventions have been particularly shown and described with reference to preferred embodiments thereof, it will be understood to those skilled in the art that various changes in form and details may be made therein without departing from the spirit and scope of the invention as defined by the appended claims.

The following references are also incorporated herein by reference in their entirety.

1. Blodgett, M. P., Ukpabi, C. V., and Nagy, P. B., "Surface Roughness Influence on Eddy Current Electrical Conductivity Measurements," Materials Evaluation, June 2003.
2. Goldfine, N., "Characterization of Shot Peening using Eddy Current MWM Sensors and Imaging MWM-Arrays," 2004 U.S. Shot Peening and Blast Cleaning Workshop, Dearborn, Mich., October, 2004.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for assessing cold work process quality of a test material comprising:
   a) placing an eddy current sensor proximate to a surface of the test material prior to cold working;
   b) measuring a sensor response at a plurality of registered positions along the surface;
   c) combining the sensor response with position information to form a spatial response in at least one dimension;
   d) cold working the material;
   e) after cold working, obtaining responses by repeating steps b) and c); and
   f) assessing cold work quality by comparing the responses obtained before and after cold working at the registered positions.

2. The method as claimed in claim 1:
   wherein the sensor response is measured at the same plurality of registered positions for the spatial response before and after cold working.

3. The method as claimed in claim 1 wherein the cold work process is shot peening and the response is a two-dimensional image of a property.

4. The method as claimed in claim 1 wherein the cold work quality is measured in terms of coverage.

5. The method as claimed in claim 4 wherein the cold work quality is measured in terms of uniformity of cold work intensity.

6. The method as claimed in claim 1 wherein the cold work quality is measured in a manner correlated with an alternate scale for cold work intensity such as residual stress or Almen intensity.

7. The method as claimed in claim 1 wherein the test material is a nickel alloy.

8. The method as claimed in claim 1 wherein the sensor measurement is performed at a single excitation frequency.

9. The method as claimed in claim 1 wherein the sensor measurement is performed at multiple excitation frequencies.

10. The method as claimed in claim 1 wherein the sensor response corrects for roughness variation.

11. The method as claimed in claim 1 further comprising converting the sensor response to a property value using a physics based model.

12. The method as claimed in claim 11 where the conversion is made using a precomputed database of sensor responses at one or more excitation frequencies.

13. The method as claimed in claim 1 wherein the sensor is a flexible array that can conform to the complex surface geometries.

14. The method as claimed in claim 13 wherein the test material is an engine component and the responses are two-dimensional images of a property related to cold work quality.

15. The method as claimed in claim 1 wherein local outlier sensor responses are suppressed or removed so that an average sensor response without the outlier values can be recorded.

16. The method as claimed in claim 1 further including assessing cold work variations across a surface of the test material as a function of spatial resolution of the sensor response.

17. The method as claimed in claim 1 wherein the cold work includes burnishing.

18. The method as claimed in claim 1 further including detecting cracks as a function of the eddy current sensor response.

* * * * *